(12) United States Patent
Shuber et al.

(10) Patent No.: US 7,981,612 B2
(45) Date of Patent: *Jul. 19, 2011

(54) METHODS OF SCREENING FOR SUPRACOLONIC NEOPLASMS BASED ON STOOL SAMPLES CONTAINING A NUCLEIC ACID MARKER INDICATIVE OF A NEOPLASM

(75) Inventors: Anthony P. Shuber, Mendon, MA (US); David A. Alquist, Rochester, MN (US)

(73) Assignees: Mayo Foundation for Medical Education and Research, Rochester, MN (US); Exact Sciences Corporation, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/042,988

(22) Filed: Mar. 5, 2008

(65) Prior Publication Data

US 2008/0254547 A1 Oct. 16, 2008

Related U.S. Application Data

(63) Continuation of application No. 10/149,464, filed as application No. PCT/US00/42683 on Dec. 7, 2000, now Pat. No. 7,368,233.

(60) Provisional application No. 60/169,457, filed on Dec. 7, 1999, provisional application No. 60/196,074, filed on Apr. 10, 2000.

(51) Int. Cl.
*C12Q 1/68* (2006.01)
*C12P 19/34* (2006.01)

(52) U.S. Cl. .......................................... 435/6; 435/91.2
(58) Field of Classification Search .............. 435/6, 91.2
See application file for complete search history.

(56) References Cited

U.S. PATENT DOCUMENTS

| | | | |
|---|---|---|---|
| 3,413,464 A | 11/1968 | Kamentsky |
| 4,101,279 A | 7/1978 | Aslam |
| 4,309,782 A | 1/1982 | Paulin |
| 4,333,734 A | 6/1982 | Fleisher |
| 4,358,535 A | 11/1982 | Falkow et al. |
| 4,445,235 A | 5/1984 | Slover et al. |
| 4,535,058 A | 8/1985 | Weinberg et al. |
| 4,578,358 A | 3/1986 | Oksman et al. |
| 4,683,195 A | 7/1987 | Mullis et al. |
| 4,683,202 A | 7/1987 | Mullis |
| 4,705,050 A | 11/1987 | Markham |
| 4,735,905 A | 4/1988 | Parker |
| 4,786,718 A | 11/1988 | Weinberg et al. |
| 4,857,300 A | 8/1989 | Maksem |
| 4,871,838 A | 10/1989 | Bos et al. |
| 4,935,342 A | 6/1990 | Seligson et al. |
| 4,981,783 A | 1/1991 | Augenlicht |
| 4,982,615 A | 1/1991 | Sultan et al. |
| 5,087,617 A | 2/1992 | Smith |
| 5,126,239 A | 6/1992 | Livak et al. |
| 5,137,806 A | 8/1992 | LeMaistre et al. |
| 5,149,506 A | 9/1992 | Skiba et al. |
| 5,196,167 A | 3/1993 | Guadagno et al. |
| 5,200,314 A | 4/1993 | Urdea |
| 5,248,671 A | 9/1993 | Smith |
| 5,272,057 A | 12/1993 | Smulson et al. |
| 5,302,509 A | 4/1994 | Cheeseman |
| 5,330,892 A | 7/1994 | Vogelstein et al. |
| 5,331,973 A | 7/1994 | Fiedler et al. |
| 5,348,855 A | 9/1994 | Dattagupta et al. |
| 5,352,775 A | 10/1994 | Albertsen et al. |
| 5,362,623 A | 11/1994 | Vogelstein et al. |
| 5,369,004 A | 11/1994 | Polymeropoulos et al. |
| 5,378,602 A | 1/1995 | Polymeropoulos et al. |
| 5,380,645 A | 1/1995 | Vogelstein |
| 5,380,647 A | 1/1995 | Bahar |
| 5,382,510 A | 1/1995 | Levine et al. |
| 5,409,586 A | 4/1995 | Kamahori et al. |
| 5,416,025 A | 5/1995 | Krepinsky et al. |
| 5,458,761 A | 10/1995 | Kamahori et al. |
| 5,463,782 A | 11/1995 | Carlson et al. |
| 5,466,576 A | 11/1995 | Schulz et al. |
| 5,468,610 A | 11/1995 | Polymeropoulos et al. |
| 5,468,613 A | 11/1995 | Erlich et al. |
| 5,482,834 A | 1/1996 | Gillespie |
| 5,489,508 A | 2/1996 | West et al. |
| 5,492,808 A | 2/1996 | de la Chapelle et al. |
| 5,496,470 A | 3/1996 | Lenhart |
| 5,506,105 A | 4/1996 | Haydock |
| 5,508,164 A | 4/1996 | Kausch et al. |
| 5,512,441 A | 4/1996 | Ronal |
| 5,514,547 A | 5/1996 | Balazs et al. |
| 5,527,676 A | 6/1996 | Vogelstein et al. |

(Continued)

FOREIGN PATENT DOCUMENTS

AU A-11325/95 10/1994

(Continued)

OTHER PUBLICATIONS

Saiki et al., Science 239, 487-491 (1988).*

(Continued)

*Primary Examiner* — Kenneth R. Horlick
(74) *Attorney, Agent, or Firm* — Casimir Jones SC

(57) ABSTRACT

The invention provides methods and materials for detecting supracolonic aerodigestive premalignant and malignant neoplasms. Specifically, the invention provides methods and materials for determining whether a stool sample from a mammal contains a neoplasm-specific marker from a neoplasm located in the supracolonic aerodigestive tissue of a mammal.

17 Claims, 13 Drawing Sheets

U.S. PATENT DOCUMENTS

| | | | |
|---|---|---|---|
| 5,532,108 | A | 7/1996 | Vogelstein |
| 5,538,851 | A | 7/1996 | Fach et al. |
| 5,559,014 | A | 9/1996 | Estes et al. |
| 5,580,729 | A | 12/1996 | Vogelstein |
| 5,589,335 | A | 12/1996 | Kearney et al. |
| 5,599,662 | A | 2/1997 | Respess |
| 5,612,473 | A | 3/1997 | Wu et al. |
| 5,635,352 | A | 6/1997 | Urdea et al. |
| 5,641,628 | A | 6/1997 | Bianchi |
| 5,645,995 | A | 7/1997 | Kieback |
| 5,670,325 | A | 9/1997 | Lapidus et al. |
| 5,688,643 | A | 11/1997 | Oka et al. |
| 5,709,998 | A | 1/1998 | Kinzler et al. |
| 5,710,028 | A | 1/1998 | Eyal et al. |
| 5,741,650 | A | 4/1998 | Lapidus et al. |
| 5,759,777 | A | 6/1998 | Kearney et al. |
| 5,830,665 | A | 11/1998 | Shuber et al. |
| 5,846,710 | A | 12/1998 | Bajaj |
| 5,856,104 | A | 1/1999 | Chee et al. |
| 5,882,865 | A | 3/1999 | Vogelstein et al. |
| 5,888,778 | A | 3/1999 | Shuber |
| 5,910,407 | A | 6/1999 | Vogelstein et al. |
| 5,916,744 | A | 6/1999 | Taylor |
| 5,928,870 | A | 7/1999 | Lapidus et al. |
| 5,942,396 | A | 8/1999 | Shiff et al. |
| 5,952,178 | A | 9/1999 | Lapidus et al. |
| 5,976,800 | A | 11/1999 | Lau et al. |
| 6,020,137 | A | 2/2000 | Lapidus et al. |
| 6,037,465 | A | 3/2000 | Hillebrand et al. |
| 6,084,091 | A | 7/2000 | Muller et al. |
| 6,100,029 | A | 8/2000 | Lapidus et al. |
| 6,143,529 | A | 11/2000 | Lapidus et al. |
| 6,146,828 | A | 11/2000 | Lapidus |
| 6,150,100 | A | 11/2000 | Ruschoff et al. |
| 6,177,251 | B1 | 1/2001 | Vogelstein et al. |
| 6,203,993 | B1 | 3/2001 | Shuber et al. |
| 6,214,187 | B1 | 4/2001 | Hammond et al. |
| 6,214,558 | B1 | 4/2001 | Shuber et al. |
| 6,235,474 | B1 * | 5/2001 | Feinberg ......................... 435/6 |
| 6,238,927 | B1 | 5/2001 | Abrams et al. |
| 6,251,660 | B1 | 6/2001 | Muir et al. |
| 6,268,136 | B1 | 7/2001 | Shuber et al. |
| 6,280,947 | B1 | 8/2001 | Shuber et al. |
| 6,300,077 | B1 | 10/2001 | Shuber et al. |
| 6,303,304 | B1 | 10/2001 | Shuber et al. |
| 6,351,857 | B2 | 3/2002 | Slaon, III et al. |
| 6,406,857 | B1 | 6/2002 | Shuber et al. |
| 6,415,455 | B1 | 7/2002 | Slaon, III et al. |
| 6,428,964 | B1 | 8/2002 | Shuber |
| 6,448,002 | B1 | 9/2002 | Hillebrand et al. |
| 6,475,738 | B2 | 11/2002 | Shuber et al. |
| 6,482,595 | B2 | 11/2002 | Shuber et al. |
| 6,498,012 | B2 | 12/2002 | Laken |
| 6,503,718 | B2 | 1/2003 | Shuber et al. |
| 6,551,777 | B1 | 4/2003 | Shuber et al. |
| 2001/0018180 | A1 | 8/2001 | Shuber et al. |
| 2002/0025525 | A1 | 2/2002 | Shuber |
| 2002/0110810 | A1 | 8/2002 | Shuber |
| 2002/0119469 | A1 | 8/2002 | Shuber et al. |
| 2002/0119472 | A1 | 8/2002 | Lapidus et al. |
| 2002/0132251 | A1 | 9/2002 | Shuber |
| 2002/0164631 | A1 | 11/2002 | Shuber et al. |
| 2003/0044780 | A1 | 3/2003 | Lapidus et al. |
| 2003/0049659 | A1 | 3/2003 | Lapidus et al. |
| 2003/0087258 | A1 | 5/2003 | Shuber |

FOREIGN PATENT DOCUMENTS

| | | | |
|---|---|---|---|
| AU | 711754 | | 7/1997 |
| AU | 704696 | | 8/1997 |
| AU | 745862 | | 9/1998 |
| AU | 744746 | | 1/1999 |
| AU | 720489 | | 9/1999 |
| AU | 199942333 | A1 | 9/1999 |
| CA | 2228769 | | 2/1997 |
| CA | 2211702 | | 5/1999 |
| DE | 195 30 132 | A1 | 2/1997 |
| DE | 195 30 132 | C2 | 2/1997 |
| DE | 197 12 332 | A1 | 10/1998 |
| DE | 197 36 691 | A1 | 2/1999 |
| EP | 0 270 017 | A2 | 6/1988 |
| EP | 0 270 017 | A3 | 6/1988 |
| EP | 0 284 362 | A2 | 9/1988 |
| EP | 0 284 362 | A3 | 9/1988 |
| EP | 0 337 498 | A2 | 10/1989 |
| EP | 0 390 323 | A2 | 10/1990 |
| EP | 0 390 323 | A3 | 10/1990 |
| EP | 0 391 565 | B1 | 10/1990 |
| EP | 0 407 789 | A1 | 1/1991 |
| EP | 0 407 789 | BI | 1/1991 |
| EP | 0 608 004 | A2 | 7/1994 |
| EP | 0 259 031 | B1 | 11/1994 |
| EP | 0 648 845 | A2 | 4/1995 |
| EP | 0 664 339 | A1 | 7/1995 |
| GB | 2327497 | A | 1/1999 |
| JP | 10323199 | | 12/1998 |
| JP | 3325270 | | 9/2002 |
| WO | WO 90/09455 | | 8/1990 |
| WO | WO 92/13103 | | 8/1992 |
| WO | WO 92/16657 | | 10/1992 |
| WO | WO 93/18186 | | 9/1993 |
| WO | WO 93/20233 | | 10/1993 |
| WO | WO 93/20235 | | 10/1993 |
| WO | WO 94/00603 | | 1/1994 |
| WO | WO 94/01447 | | 1/1994 |
| WO | WO 94/09161 | | 4/1994 |
| WO | WO 94/10575 | | 5/1994 |
| WO | WO 94/11383 | | 5/1994 |
| WO | WO 95/00669 | | 1/1995 |
| WO | WO 95/07361 | | 3/1995 |
| WO | WO 95/09928 | | 4/1995 |
| WO | WO 95/09929 | | 4/1995 |
| WO | WO 95/12606 | | 5/1995 |
| WO | WO 95/13397 | | 5/1995 |
| WO | WO 95/15400 | | 6/1995 |
| WO | WO 95/16792 | | 6/1995 |
| WO | WO 95/18818 | | 7/1995 |
| WO | WO 95/19448 | | 7/1995 |
| WO | WO 95/25813 | | 9/1995 |
| WO | WO 95/31728 | | 11/1995 |
| WO | WO 96/01907 | | 1/1996 |
| WO | WO 96/06951 | | 3/1996 |
| WO | WO 96/08514 | | 3/1996 |
| WO | WO 96/12821 | | 5/1996 |
| WO | WO 96/13611 | | 5/1996 |
| WO | WO 96/23895 | A | 8/1996 |
| WO | WO 96/29430 | A | 9/1996 |
| WO | WO 96/30545 | | 10/1996 |
| WO | WO 97/07239 | | 2/1997 |
| WO | WO 97/09449 | | 3/1997 |
| WO | WO 97/09600 | | 3/1997 |
| WO | WO 97/19191 | A | 5/1997 |
| WO | WO 97/23651 | | 7/1997 |
| WO | WO 97/25442 | | 7/1997 |
| WO | WO 97/28450 | | 8/1997 |
| WO | WO 98/08971 | | 3/1998 |
| WO | WO 98/38338 | | 9/1998 |
| WO | WO 98/39478 | | 9/1998 |
| WO | WO 98/58081 | | 12/1998 |
| WO | WO 98/58084 | | 12/1998 |
| WO | WO 99/07894 | | 2/1999 |
| WO | WO 99/07895 | | 2/1999 |
| WO | WO 99/10528 | | 3/1999 |
| WO | WO 99/20798 | | 4/1999 |
| WO | WO 99/26724 | | 6/1999 |
| WO | WO 99/28507 | | 6/1999 |
| WO | WO 99/45374 | | 9/1999 |
| WO | WO 99/53316 | | 10/1999 |
| WO | WO 99/55912 | | 11/1999 |
| WO | WO 99/66077 | | 12/1999 |
| WO | WO 99/66078 | | 12/1999 |
| WO | WO 99/66079 | | 12/1999 |
| WO | WO 00/09751 | | 2/2000 |
| WO | WO 00/11215 | | 3/2000 |
| WO | WO 00/31298 | | 6/2000 |
| WO | WO 00/31303 | | 6/2000 |
| WO | WO 00/31305 | | 6/2000 |

| | | |
|---|---|---|
| WO | WO 00/32820 | 6/2000 |
| WO | WO 00/50640 | 8/2000 |
| WO | WO 00/50870 | 8/2000 |
| WO | WO 00/58514 A3 | 10/2000 |
| WO | WO 00/60118 | 10/2000 |
| WO | WO 00/61808 A3 | 10/2000 |
| WO | WO 00/66005 | 11/2000 |
| WO | WO 00/70096 | 11/2000 |
| WO | WO 00/70096 A3 | 11/2000 |
| WO | WO01/11083 A2 | 2/2001 |
| WO | WO01/11083 A3 | 2/2001 |
| WO | WO 01/18252 A2 | 3/2001 |
| WO | WO 01/42502 A2 | 6/2001 |
| WO | WO 01/42503 A2 | 6/2001 |
| WO | WO 01/42781 A2 | 6/2001 |
| WO | WO01/64950 A2 | 9/2001 |
| WO | WO01/64950 A3 | 9/2001 |
| WO | WO02/055740 A2 | 7/2002 |
| WO | WO02/059379 A2 | 8/2002 |
| WO | WO02/074995 A1 | 9/2002 |
| WO | WO02/092858 A2 | 11/2002 |

OTHER PUBLICATIONS

Aaltonen et al. (1994) "Replication Errors in Benign and Malignant Tumors from Hereditary Nonpolyposis Colorectal Cancer Patients" *Cancer Research* 54:1645-1648.

Aaltonen et al. (1998) "Incidence of Hereditary Nonpolyposis Colorectal Cancer and the Feasibility of Molecular Screening for the Disease" *The New England Journal of Medicine* 338:1481-1487.

Ausubel et al., (1995), *Short Protocols in Molecular Biology*, 3d ed., pp. 2-3-2-12, 3-30-3-33.

Bertario et al. (1999) "Risk of Colorectal Cancer Following Colonoscopic Polypectomy" *Tumori* 85:157-162.

Beskin et al., (1995), "On the Mechanism of the Modular Primer Effect," *Nucleic Acids Research*, vol. 23, No. 15, 2881-2885.

Blum H.E., (1995) "Colorectal Cancer: Future Population Screening for Early Colorectal Cancer" *European Journal of Cancer*, vol. 31A, pp. 1369-1372.

Bos et al., (May 28, 1987) "Prevalence of *ras* Gene Mutations in Human Colorectal Cancers," *Nature*, vol. 327, pp. 293-297.

Caldas et al., (Jul. 1, 1994) "Detection of K-ras Mutations in the Stool of Patients with Pancreatic Adenocarcinoma and Pancreatic Ductal Hyperplasia" *Cancer Research*, vol. 54, pp. 3568-3573.

Capozzi et al. (1999) "Evaluation of the Replication Error Phenotype in Relation to Molecular and Clinicopathological Features in Hereditary and Early Onset Colorectal Cancer" *European Journal of Cancer* 35: 289-295.

Cave et al., (1994) "Realiability of PCR Directly from Stool Samples: Usefulness of an Internal Standard," *BioTechniques*, vol. 16, No. 5, pp. 809-810.

Chapelle (1999) "Testing Tumors for Microsatellite Instability" *European Journal of Human Genetics* 7:404-408.

Charlesworth et al., (Sep. 15, 1994) "The Evolutional Dynamics of Repetitive DNA in Eukaryotes," *Nature*, vol. 371, pp. 215-220.

Chen et al. (1997) "Microsatellite Instability in Sporadic-Colon-Cancer Patients With and Without Liver Metastases" *International Journal of Cancer* 74:740-474.

Coll et al., (Oct. 1989) "Evaluation of a Rapid Method of Extracting DNA from Stool Samples for Use in Hybridization Assays," *Journal of Clinical Microbiology*, vol. 27, No. 10, pp. 2245-2248.

Coughlin et al. (1999) "Public Health Perspectives on Testing for Colorectal Cancer Susceptibility Genes" *American Journal of Preventive Medicine* 16:99-104.

Cunningham C. and M.G. Dunlop, (1996) "Molecular Genetic Basis of Colorectal Cancer Susceptibility," *British Journal of Surgery*, vol. 83, pp. 321-329.

Deng et al., (Dec. 20, 1996) "Loss of Heterozygosity in Normal Tissue Adjacent to Breast Carcinomas," *Science*, vol. 274, pp. 2057-2059.

Deuter et al., (1995) "A Method for Preparation of Fecal DNA Suitable for PCR," *Nucleic Acids Research*, vol. 23, No. 18, pp. 3800-3801.

Dib et al., (Mar. 14, 1996) "A Comprehensive Genetic Map of the Human Genome Based on 5,264 Microsatellites," *Nature* vol. 380, pp. 152-154.

Duffy M.J., (1995) "Can Molecular Markers Now be Used for Early Diagnosis of Malignancy?" *Clin. Chem.*, vol. 41, No. 10, pp. 1410-1413.

Eguchi et al., (Apr. 15, 1996) "Mutations of the p53 Gene in the Stool of Patients with Resectable Colorectal Cancer," *Cancer Supplement*, vol. 77, No. 8, pp. 1707-1710.

Enari et al., (Jan. 1, 1998) "A Caspase-Activated DNase that Degrades DNA During Apoptosis, and its Inhibitor ICAD," *Nature*, vol. 391, pp. 43-50.

Fearon, E.R., (1995) "16 Molecular Abnormalities in Colon and Rectal Cancer," *The Molecular Basis of Cancer*, pp. 340-357.

Grossman et al. (1988), "Colonoscopic Screening of persons With Suspected Risk Factors for Colon Cancer" *Gastroenterology* 94:395-400.

Gyllensten U. B., Allen M., (1995) "Sequencing of In Vitro Amplified DNA," *Recombinant DNA Methodology II*, (Wu, ed.), pp. 565-578.

Hasegawa et al., (1995) "Detection of K-ras Mutations in DNAs Isolated From Feces of Patients with Colorectal Tumors by Mutant-Allele-Specific Amplification (MASA)," *Oncogene*, vol. 10, pp. 1441-1445.

Hoang et al. (1997) "BAT-26, an Indicator of the Replication Error Phenotype in Cancers and Colorectal Cell Lines" *Cancer Research* 57:300-303.

Honchel et al., (1995) "Genomic Instability in Neoplasia," *Seminars in Cell Biology*, vol. 6, pp. 45-52.

Hoss et al., (Sep. 17, 1992) "Excrement Analysis by PCR" *Scientific Correspondence* pp. 199.

Iino et al. (1999) "DNA Microsatellite Instability in Hyperplastic Polyps, Serrated Adenomas, and Mixed Polyps: a Mild Mutator Pathway for Colorectal Cancer?" *Journal of Clinical Pathology* 52:5-9.

Iniesta et al. (1998) "Genetic Abnormalities and Microsatellite Instability in Colorectal Cancer" *Cancer Detection and Prevention* 22:383-395.

Ishimaru et al. (1995) "Microsatellite Instability in Primary and Metastatic Colorectal Cancers" *International Journal of Cancer* 64:153-157.

Jarvinen et al. (1995) "Screening Reduces Colorectal Cancer Rate in Families With Hereditary Nonpolyposis Colorectal Cancer" *Gastroenterology* 108:1405-1411.

Jernvall et al. (1999) "Microsatellite Instability: Impact on Cancer Progression in Proximal and Distal Colorectal Cancers" *European Journal of Cancer* 35:197-201.

Jessup J.M. and G.E. Gallick, (Sep./Oct. 1992) "The Biology of Colorectal Carcinoma," *Current Problems in Cancer*, pp. 263-328.

Jonsson et al., (Jan. 1995) "From Mutation Mapping to Phenotype Cloning," *Proc. Natl. Acad. Sci.*, vol. 92, pp. 83-85.

Kim et al., (1998) "Microsatellite Instability in Young Patients With Colorectal Cancer" *Pathology International* 48:586-594.

Konishi et al. (1996) "Molecular Nature of Colon Tumors in Hereditary Nonpolyposis Colon Cancer, Familial Polyposis, and Sporadic Colon Cancer" *Gastroenterology* 111:307-317.

Lamberti et al. (1999) "Microsatellite Instability—A Useful Diagnostic Tool to Select Patients at High Risk for Hereditary Non-Polyposis Colorectal Cancer: A Study in Different Groups of Patients With Colorectal Cancer" *Gut* 44:839-843.

Lengauer et al., (Dec. 17, 1998) "Genetic Instabilities in Human Cancers," *Nature*, vol. 396, pp. 643-649.

Leong et al., (1993) "Detection of MYCN Gene Amplification and Deletions of Chromosome 1p in Neuroblastoma by In Situ Hybridization Using Routine Histologic Sections," *Laboratory Investigations*, vol. 69, No. 1, pp. 43-50.

Lin et al. (1998) "Colorectal and Extracolonic Cancer Variations in MLH1/MSH2 Hereditary Nonpolyposis Colorectal Cancer Kindreds and the General Population" *Diseases of the Colon & Rectum* 41:428-433.

Litia et al., (1992) "Simultaneous Detection of Two Cystic Fibrosis Alleles Using Dual-Label Time-Resolved Fluorometry,"0 *Molecular and Cellular Probes*, vol. 6, pp. 505-512.

Lleonart et al. (1998) "Microsatellite Instability and p53 Mutations in Sporadic Right and Left Colon Carcinoma" *American Cancer Society* 83:889-895.

Loktionov A. and I. K. O'Neill, (1995) "Early Detection of Cancer-Associated Gene Alterations in DNA Isolated from Rat Feces During Intestinal Tumor Induction with 1,2-Dimethylhydrazine," *International Journal of Oncology*, vol. 6, pp. 437-445.

Loktionov et al., (Feb. 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337-341.

Mao L. et al., (Feb. 2, 1996) "Molecular Detection of Primary Bladder Cancer by Microsatellite Analysis," *Science*, vol. 271, pp. 659-662.

Myers, R.M., (Feb. 12, 1993) "The Pluses of Subtraction," *Science*, vol. 259, pp. 942-943.

Naber S. P., (Dec. 1, 1994) "Molecular Pathology—Detection of Neoplasia," *New England Journal of Medicine*, vol. 331, No. 22, pp. 1508-1510.

Nollau et al., (May 1996) "Isolation of DNA from Stool and Bodily Fluids for PCR Amplification," *BioTechniques*, vol. 20, No. 5, pp. 784-788.

Nollau et al., (1996) "Detection of K-ras Mutations in Stools of Patients with Colorectal Cancer by Mutant-Enriched PCR," *Int. J. Cancer*, vol. 66, pp. 332-336.

Orlow I., et al., (Oct. 18, 1995) "Deletion of the p16 and p15 Genes in Human Bladder Tumors *Journal of the National Cancer Institute*," vol. 87, No. 20, pp. 1524-1529.

Orou, et al., (1995) "Allele-Specific Competitive Blocker PCR: A One-Step Method With Applicability to Pool Screening" *Human Mutation* vol. 6, 163-169.

Park et al. (1999) "Gene-Environment Interaction in Hereditary Nonpolyposis Colorectal Cancer with Implications for Diagnosis and Genetic Testing" *International Journal of Cancer* 82:516-519.

Pletomaki et al. (1997) "Mutations Predisposing to Hereditary Nonpolyposis Colorectal Cancer: Database and Results of a Collaborative Study" *Gastroenterology* 113:1146-1158.

Pharmacia, (1998) *BioDirectory*, pp. 104-109.

Pharmacia, (1991/1992) *Molecular and Cell Biology Catalogue*, pp. 8.3-8.6.

Piao et al. (Sep. 1997) "Relationship between Loss of Heterozygosity of Tumor Suppressor Genes and Histologic Differentiation in Hepatocellular Carcinoma," *Cancer*, vol. 80, No. 5, pp. 865-872.

Ponz de Leon et al. (1998) "Frequency and Type of Colorectal Tumors in Asymptomatic High-Risk Individuals in Families with Hereditary Nonpolyposis Colorectal Cancer" *Cancer Epidemiology, Biomarkers & Prevention* 7:639-641.

Ponz de Leon et al. (1999) "Hereditary Colorectal Cancer in the General Population: From Cancer Registration to Molecular Diagnosis" *Gut* 45:32-38.

Pyatt et al. (1999) "Polymorphic Variation at the BAT-25 and BAT-26 Loci in Individuals of African Origin" *American Journal of Pathology* 155:349-353.

Raff, M., (Nov. 12, 1998) "Cell Suicide for Beginners," *Nature*, vol. 396, pp. 119-122.

Rashid et al. (1999) "Genetic Epidemiology of Mutated K-*ras* Proto-Oncogene, Altered Suppressor Genes, and Microsatellite Instability in Colorectal Adenomas" *Gut* 44:826-833.

Ravelingien et al., (1995) "Contribution of Molecular Oncology in the Detection of Colorectal Carcinomas," *Acta Gastro-Enterologica Belgica*, vol. 58, pp. 270-273.

Riegler et al. (1999) "Prevalence of HNPCC in a Series of Consecutive Patients on the First Endoscopic Diagnosis of Colorectal Cancer: A Multicenter Study" *Endoscopy* 31:337-341.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240-251.

Ridanpaa et al., (1995) "Detection of Loss of Heterozygosity in the p53 Tumor Suppressor Gene Using a PCR-based Assay," *Path. Res. Pract.*, vol. 191, pp. 399-402.

Rodriguez-Bigas et al. (1997) "A National Cancer Institute Workshop on Hereditary Nonpolyposis Colorectal Cancer Syndrome: Meeting Highlights and Bethesda Guidelines" *Journal of the National Cancer Institute* 89:1758-1762.

Salahshor et al. (1999) "Microsatellite Instability in Sporadic Colorectal Cancer is Not an Independent Prognostic Factor" *British Journal of Cancer* 81:190-193.

Samowitz et al. (1995) "Microsatellite Instability in Human Colonic Cancer Is Not a Useful Clinical Indicator of Familial Colorectal Cancer" *Gastroenterology* 109:1765-1771.

Samowitz et al. (1997) "Microsatellite Instability in Colorectal Adenomas" *Gastroenterology* 112:1515-1519.

Samowitz et al. (1999) "BAT-26 and BAT-40 Instability in Colorectal Adenomas and Carcinomas and Germline Polymorphisms" *American Journal of Pathology* 154:1637-1641.

Sanger et al., (Dec. 1977) "DNA Sequencing with Chain-Terminating Inhibitors" *Proc. Natl. Acad. Sci. USA*, vol. 74, No. 12, pp. 5463-5467.

Santagati et al., (1997) "Quantitation of Low Abundance mRNAs in Glial Cells Using Different Polymerase chain Reaction (PCR)-Based Methods," *Elsevier Science—Brain Research Protocols*, pp. 217-223.

Segel I., (1976), "Double Label Analysis," *Biochemical Calculations*, 2d ed., pp. 373-376.

Sidransky, et al., (Apr. 3, 1992) "Identification of ras Oncogene Mutations in the Stool of Patients with Curable Colorectal Tumors," *Science*, vol. 256, pp. 102-105.

Smith-Ravin et al., (1995) "Detection of c-Ki-ras Mutations in Faecal Samples from Sporadic Colorectal Cancer Patients," *Gut*, vol. 36, pp. 81-86.

Syngal et al. (1998) " Benefits of Colonoscopic Surveillance and Prophylactic Colectomy in Patients With Hereditary Nonpolyposis Colorectal Cancer Mutations" *Annals of Internal Medicine* 129:787-796.

Syngal et al. (1999) "Interpretation of Genetic Test Results for Hereditary Nonpolyposis Colorectal Cancer" *JAMA* 282:247.

Takeda et al., (1993) "Detection of K-ras Mutation in Sputum by Mutant-Allele-Specific Amplification (MASA)," *Human Mutation*, vol. 2, pp. 112-117.

Thibodeau et al., (May 7, 1993) "Microsatellite Instability in Cancer of the Proximal Colon," *Science*, vol. 260, pp. 816-819.

Vasen et al. (1993) "Surveillance in Hereditary Nonpolyposis Colorectal Cancer: An International Cooperative Study of 165 Families" *Diseases of the Colon & Rectum*) 36:1-4.

Vasen et al. (1998) "A Cost-Effectiveness Analysis of Colorectal Screening of Hereditary Nonpolyposis Colorectal Carcinoma Gene Carriers" *American Cancer Society* 82:1632-1637.

Vasen et al. (1999) "New Clinical Criteria for Hereditary Nonpolyposis Colorectal Cancer (HNPCC, Lynch Syndrome) Proposed by the International Collaborative Group on HNPCC" *Gastroenterology* 116:1453-1456.

Villa et al., (May 1996) "Identification of Subjects at Risk for Colorectal Carcinoma Through a Test Based on K-ras Determination in the Stool," *Gastroenterology*, vol. 110, No. 5, pp. 1346-1353.

Vogelstein, B. and Kinzler, K.W., (Aug. 1999) "Digital PCR," *Proc. Natl. Acad. Sci. USA*, vol. 96, pp. 9236-9241.

Wallace et al., (1979) "Hybridization of Synthetic Oligodeoxyribonucleotides to Φχ 174 DNA: the Effect of Single Base Pair Mismatch," *Nucleic Acids Research*, vol. 6, No. 11, pp. 3543-3557.

Walsh et al., (Feb. 6, 1992) "Preferential PCR Amplification of Alleles: Mechanisms and Solutions," *PCR Methods and Applications*, pp. 241-250.

Wang et al., (May 15, 1998) "Large-Scale Identification, Mapping, and Genotyping of Single-Nucleotide Olymorphisms in the Human Genome," *Science*, vol. 280, pp. 1077-1082.

Watson et al., "Isolation of Differentiality Expressed Sequence Tags from Human Breast Cancer," *Advances in Brief XP 000576043*, pp. 4598-4602.

Wijnen et al. (1999) "Familial Endometrial Cancer in Female Carriers of MSH6 Germline Mutations" *Nature Genetics* 23:142-144.

Young G.P., and B.H. Demediu, (1992) "The Genetics, Epidemiology, and Early Detection of Gastrointestinal Cancers" *Current Opinion in Oncology*, vol. 4, pp. 728-735.

Zhou et al. (1997) "Allelic Profiles of Mononucleotide Repeat Microsatellites in Control Individuals and in Colorectal Tumors With and Without Replication Errors" *Oncogene* 15:1713-1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21:101-107.

Allen et al. (1997), "Morphological and biochemical characterization and analysis of apoptosis." *J. Pharm. & Toxicol. Methods*, vol. 37, No. 4, pp. 215-228.

Ambrosini et al. "A novel anti-apoptosis gene, survivin, expressed in cancer and lymphoma" *Nature Medicine*, vol. 3, No. 8, pp. 917-921, Aug. 1997.

Anker et al., (1999), "Detection of Circulating Tumour DNA in the Blood (plasma/serum) of Cancer Patients," *Cancer and Metastasis Reviews*, vol. 18, pp. 65-73.

Arber et al. "A K-ras Oncogene Increases Resistance to Sulindac-Induced Apoptosis in Rat Enterocytes," *Gastroenterology*, vol. 113, No. 6, pp. 1892-1900, Dec. 1997.

Azhikina et al. (1996), "Factors Affecting the Priming Efficiency of Short Contiguous Oligonucleotide Strings in the Primer Walking Strategy of DNA Sequencing," *DNA Sequence* 6:211-16.

Barry et al. "Identification of Deoxyribonuclease II as an Endonucleas Involved in Apoptosis," *Archives of Biochemistry and Biophysics*, vol. 300, No. 1, pp. 440-448, Jan. 1993.

Bernstein et al. "A Bile Acid-induced Apoptosis Assay for Colon-Cancer Risk and Associated Quality Control Studies," *Cancer Research*, vol. 59, pp. 2353-2357, May 15, 1999.

Boom et al., (Mar. 1990) "Rapid and Simple Method for Purification of Nucleic Acids" *J. Clin. Microbiol.*, vol. 28, No. 3, pp. 495-503.

Croitoru et al. "Reduce, Reuse, and Recycle: Shedding Light on Shedding Cells," *Gastroenterology*, vol. 105, pp. 1243-1246, Oct. 1993.

Cawkwell et al. (1994), "Frequency of allele loss of DCC, p53, RB1, WT1, NF1, NM23 and APC/MCC in colorectal cancer assayed by fluorescent multiplex polymerase chain reaction." *Brit. J. Can.*, vol. 70, No. 5, pp. 813-818.

Chen et al., (Jul. 15, 1996), "Detection of Single-Base Mutations by a Competitive Mobility Shift Assay," *Analytical Biochemistry, US, Academic, Press*, vol. 239, No. 1, pp. 61-69.

Coombs et al., (May 21, 1996) "A Rapid, Simple, and User-Friendly Method for DNA Extraction from Clinical Stool Samples," *ASM 1996 General Meeting*, New Orleans, LA.

Dennin, (1979), "DNA of Free and Complexed Origin in Human Plasma: Concentration and Length Distribution," *Klin. Wochenschr*, vol. 57, pp. 451-456.

Depraetere, " 'Eat me' Signals of apoptotic bodies," *Nature Cell Biology*, vol. 2, p. E104, Jun. 2000.

Ditkoff et al. (1996), "Detection of circulating thyroid cells in peripheral blood." *Surgery* vol. 120, No. 6, pp. 959-965.

Eads et al., (1999) "CpG Island Hypermethylation in Human Colorectal Tumors Is Not Associated with DNA Methyltransferase Overexpression." *Cancer Research*, vol. 59, No. 10, pp. 2302-2306.

Echeverria et al., (Sep. 1985) "DNA Hybridization in the Diagnosis of Bacterial Diarrhea," *Clinics in Laboratory Medicine*, vol. 5, No. 3, Sep. 1985, pp. 447-462.

Emlen et al., (1984), "Effect of DNA Size and Strandedness on the in vivo Clearance and Organ Localization of DNA," *Clin. exp. Immunol.*, vol. 56, pp. 185-192.

Finkel "Does Cancer Therapy Trigger Cell Suicide?," *Science*, vol. 286, pp. 2256-2258, Dec. 17, 1999.

Fournie et al., (1995), "Plasma DNA as a Marker of Cancerous Cell Death. Investigations in Patients Suffering from Lung Cancer and in Nude Mice Bearing Human Tumours," *Cancer Letters*, vol. 91, pp. 221-227.

Garewal et al. "Reduced Bile Acid-induced Apoptosis in 'Normal' Colorectal Mucosa: A Potential Biological Marker for Cancer Risk," *Cancer Research*, vol. 56, pp. 1480-1483, Apr. 1, 1996.

Giacona, et al. (1998), "Cell-free DNA in Human Blood plasma: Length Measurements in Patients with Pancreatic Cancer and Healthy Controls," *Pancreas*, vol. 17, No. 1, pp. 89-97.

Halim, "Apoptosis: Orderly Dismantling," *The Scientist*, p. 19, Feb. 7, 2000.

Hall et al. "Regulation of cell number in the mammalian gastrointestinal tract: the importance of apoptosis," *Journal of Cell Science*, vol. 107, pp. 3569-3577, 1994.

Hetts, "To Die or Not to Die, An Overview of Apoptosis and Its Role in Disease," *JAMA*, vol. 279, No. 4, pp. 300-307, Jan. 28, 1998.

Hibi et al., (Apr. 1998), "Molecular Detection of Genetic Alterations in the Serum of Colorectal Cancer Patients," *Cancer Research*, vol. 58, pp. 1405-1407.

Hitchcock, "Actin- Deoxyribonuclease I Interaction," *The Journal of Biochemical Chemistry*, vol. 255, No. 12, pp. 5668-5673, 1980.

Hunsaker, et al. (1989), "Use of Reversible Target Capture to Detect Subattomole Quantities of Target Nonradioleotopically in Crude Specimens in One Hour," *Abstracts of the 89th Meeting of the American Society for Microbiology*, D-169, p. 110.

Ito et al., (1999), "Profile of Circulating Levels of Interleukin-1 Receptor Antagonist and Interleukin-6 in Colorectal Cancer Patients," *Scand. J. Gastroenterol.*, vol. 11, pp. 1139-1143.

Iwanaga et al. "A Novel Mechanism for Disposing of Effete Epithelial Cells in the Small Intestine of Guinea Pigs," *Gastroenterology*, vol. 105, No. 4, pp. 1089-1097, 1993.

Kataoka et al. "Association of high molecular weight DNA fragmentation with apoptotic or non-apoptotic cell death induced by calcium ionophore" *FEBS Letters*, vol. 364, pp. 264-267, 1995.

Kawasaki et al. "Inhibition of Apoptosis by Survivin Predicts Shorter Survival Rates in Colorectal Cancer," *Cancer Research*, vol. 58, pp. 5071-5074, Nov. 15, 1998.

Kishi et al. "Human Serum Deoxyribonuclease I (DNase I) Polymorphism: Pattern Similarities among Isozymes from Serum, Urine, Kidney, Liver, and Pancreas," *Am. J. Hum. Genet.*, vol. 47, pp. 121-126, 1990.

Komano et al. "Homeostatic regulation of intestinal epithelia by intraepithelial γδ T cells" *Proc. Natl. Acad. Sci. USA 92*, vol. 92, pp. 6147-6151, Jun. 1995.

Lefrere et al., (Oct. 1998) "Screening Blood Donations for Viral Genomes: Multicenter Study of Real-Time Simulation Using Pooled Samples on the Model of HCV RNA Detection," *Transfusion*, vol. 38, pp. 915-923.

Leon et al., (Mar. 1977), "Free DNA in the Serum of Cancer Patients and the Effect of Therapy," *Cancer Research*, vol. 37, pp. 646-650.

Li et al., (Aug. 1996) "Rapid Detection of Mycobacterium Avium in Stool Samples from AIDS Patients by Immunomagnetic PCR," *J. Clin. Microbiol.*, vol. 34, No. 8, pp. 1903-1907.

Lipkin, "Biomarkers of Increased Susceptibility to Gastrointestinal Cancer: New Application to Studies of Cancer Prevention in Human Subjects," *Cancer Research*, vol. 48, pp. 235-245, Jan. 15, 1998.

Maebo, (1990), "Plasma DNA Level as a Tumor Marker in Primary Lung Cancer," Japanese; English abstract attached.

Mannherz et al. "A Specific 1:1 G-Actin: DNAase I Complex Formed by the Action of DNAase I on F-Actin," *FEBS Letters*, vol. 60, No. 1, pp. 34-38, Dec. 1975.

Mannherz et al. "The Interaction of Bovine Pancreatic Deoxyribonuclease I and Skeletal Muscle Actin," *Eur. J. Biochem*, vol. 104, pp. 367-379, 1980.

Metspalu A., "Arrayed Primer Extension (APEX) for Mutation Detection Using Gene-Specific DNA Chips" *European Society of Human Genetics*, vol. 6, No. Sup 1, 1998, p. PL36 XP000892253 Abstract.

Morandi et al., (Jun. 1998) "Detection of HIV Type 1 RNA in Pools of Sera Negative for Antibodies to HIV-1 and HIV-2," *J. of Clinical Microbiology*, vol. 36, No. 6, pp. 1534-1538.

Morrissey et al., (May 14-18, 1989) "Novel Hybridization Technique with Subattomole Sensitivity in Specimens," *American Society for Microbiology*, 89th Annual Meeting, Abstract D-168, p. 110.

Morrissey, et al., (Sep. 1989) "Nucleic Acid Hybridization Assays Employing dA-Tailed Capture Probes," *Analytical Biochemistry*, vol. 181, No. 2, pp. 345-359.

Morrissey, D. and Collins, M., (Jun. 1989) "Nucleic Acid Hybridization Assays Employing dA-Tailed Capture Probes: Single Capture Methods," *Mol. And Cell. Probes*, vol. 3, No. 2, pp. 189-207.

Mulcahy et al. (1998), "A prospective study of K-ras mutations in the plasma of pancreatic cancer patients," *Clin. Cancer Res.*, vol. 4, pp. 271-275.

Olive, (Feb. 1989) "Detection of Enterotoxigenic *Escherichia coli* after Polymerase Chain Reaction Amplification with a Thermostable DNA Polymerase," *Journal of Clinical Microbiology*, vol. 27, No. 2, pp. 261-265.

Paabo et al., (1988) "Mitochondrial DNA Sequences from a 7000-year old Brain," *Nucleic Acids Research*, vol. 16, No. 20, pp. 9775-9787.

Pacek et al., (May 1993)"Determination of Allele Frequencies at Loci with Length Polymorphism by Quantitative Analysis of DNA Amplified from Pooled Samples," *PCR Methods and Applications*, vol. 2, No. 4, pp. 313-317.

Park et al. "Detergent and Enzyme Treatment of Apoptotic Cells for Observation of DNA Fragmentation," *BioTechniques*, vol. 24, No. 4, pp. 558-559, 1998.

Payne et al. "Role of Apoptosis in Biology and Pathology: Resistance to Apoptosis in Colon Carcinogenesis," *Ultrastructural Pathology*, vol. 19, pp. 221-248, 1995.

Peitsch et al. "Characterization of the endogenous deoxyribonuclease involved in nuclear DNA degradation during apoptosis (programmed cell death)," *The EMBO Journal*, vol. 12, No. 1, pp. 371-377, 1993.

Peitsch et al. "Functional characterisation of serum DNase I in MRI," *Biochemical and Biophysical Research Communications*, vol. 186, No. 2, pp. 739-745, Jul. 31, 1992.

Peitsch et al. "The apoptosis endonucleases: cleaning up after cell death?," *Trends in Cell Biology*, vol. 4, pp. 37-41, Feb. 4, 1994.

Polzar et al. "Distribution of deoxyribonuclease I in rat tissues and its correlation to cellular turnover and apoptosis (programmed cell death)," *European Journal of Cell Biology*, vol. 64, pp. 200-210, 1994.

Polzar et al. "Overexpression of deoxyribonuclease I (DNase I) transfected into COS-cells: its distribution during apoptotic cell death," *European Journal of Cell Biology*, vol. 62, pp. 397-405, 1993.

Raptis et al., (Dec. 1980), "Quantitation and Characterization of Plasma DNA in Normals and Patients with Systemic Lupus Erythematosus," *J. Clin. Invest.*, vol. 66, pp. 1391-1399.

Rinaldy et al. (1988), "Gene Cloning Using cDNA Libraries in a Differential Competition Hybridization Strategy: Application to Cloning XP-A Related Genes," *DNA* vol. 7, No. 8, pp. 563-570.

Ruzicka et al., (1992) "Apolipoprotein Allele Specific PCR: Large-Scale Screening of Pooled Blood Samples," *J. of Lipid Research*, vol. 33, pp. 1563-1567.

Saitoh et al. "Analysis of Bcl-2, Bax and Survivin genes in uterine cancer," *International Journal of Oncology*, vol. 15, pp. 137-141, 1999.

Sales et al., (Jul. 31, 1999), "Blood Dissemination of Colonic Epithelial Cells During No-touch Surgery for Rectosigmoid Cancer," *The Lancet*, vol. 354, p. 392.

Samiotaki et al. (1994), "Dual-Color Detection of DNA Sequence Variants by Ligase-Mediated Analysis," *Genomics* 20:238-42.

Schmitt et al. (1998), "Bax-alpha promotes apoptosis induced by cancer chemotherapy and accelerates the activation of caspase 3-like cysteine proteases in p53 double mutant B lymphoma Namalwa cells," *Cell Death & Diff.*, vol. 5, No. 6, pp. 506-516.

Sen "Programmed Cell Death: Concept, Mechanism and Control," *Biol. Rev.*, vol. 67, pp. 287-319, 1992.

Shapiro et al., (Jun. 1, 1983), "Determination of Circulating DNA Levels in Patients with Benign or Malignant Gastrointestinal Disease," *Cancer*, vol. 51, No. 11, pp. 2116-2120.

Shaw et al., (1998) "Allele Frequency Distribution in Pooled DNA Samples, Applications to Mapping Complex Disease Genes," *Genome Research*, vol. 8, pp. 111-123.

Sidransky, D. (1997) "Nucleic acid-based methods for the detection of cancer," *Science*, vol. 278, No. 5340, pp. 1054-1058.

Skoletsky et al. (1998) "High frequency of detecting amplifiable DNA in stools of apparently normal individuals," *Gastroenterology*, vol. 114, No. 4, p. A681.

Sträter et al. "Rapid Onset of Apoptosis In Vitro Follows Disruption of B1 Integrin/Matrix Interactions in Human Colonic Crypt Cell" *Gastroenterology*, vol. 110, No. 6, pp. 1776-1784, Jun. 1996.

Stroun et al., (1987), "Isolation and Characterization of DNA from the Plasma of Cancer Patients," *Eur. J. Cancer Clin. Oncol.*, vol. 23, No. 6, pp. 707-712.

Tompkins et al., (1986) "Approaches to the Detection of Enteric Pathogens, Including *Campylobacter*, using Nucleic Acid Hybridization," *Diagn. Microbiol, Infect. Dis.*, vol. 4, pp. 71S-78S.

Tsujitani et al. "Apoptotic Cell Death and Its Relationship to Carcinogenesis in Colorectal Carcinoma," *Cancer Supplement*, vol. 77, No. 8, pp. 1711-1716, Apr. 15, 1996.

Vera-Garcia, et al., (May 16-20, 1993) "Development and Evaluation of an Instrument Designed to Reproducibly Release Nucleic Acids from Microorganisms," *American Society for Microbiology: Polymerase Chain Reaction*, 93rd General Meeting, Session 214, Abstract C-217, p. 484.

Vet et al. (1998) "Comparative analysis of p53 mutations in bladder washings and histologic specimens," *Am. J. Clin. Path.*, vol. 110, No. 5, pp. 647-652.

Vogelstein et al., (1979) "Preparative and Analytical Purification of DNA from Agarose," *Proc. Natl. Acad. Sci. USA*, vol. 76, No. 2, pp. 615-619.

Wagner et al. "Regulation of Gastric Epithelial Cell Growth by Helicobacter pylori: Evidence for a Major Role of Apoptosis," *Gastroenterology*, vol. 113, No. 6, pp. 1836-1847, Dec. 1997.

Walsh et al., (1991) "Chelex® 100 as a Medium for Simple Extraction of DNA for PCR-Based Typing from Forensic Material," *BioTechniques*, vol. 10, No. 4, pp. 506-513.

Walton et al., (1997) "A PCR-Based Method for Detecting Rare Genotypes in Large Samples of Individuals," *Mol. Ecology*, vol. 6, No. 2, pp. 195-197.

Zhang et al. "Quantitative determination of apoptotic death in cultured human pancreatic cancer cells by propidium iodide and digitonin," *Cancer Letters*, vol. 142, pp. 129-137, 1999.

Ahlquist et al., "Colorectal Cancer Screening by Detection of Altered Human DNA in Stool: Feasibility Multitarget Assay Panel," Presented at Digestive Disease Week Annual Conference, Orlando, FL, May 19, 1999 (*Gastroenterology*, 119, pp. 1219-1227 (2000)).

Ahlquist et al., "Universal Detection of Aerodigestive Cancers by Assay of Nonapoptotic Human DNA in Stool," Presented at Digestive Disease Week Annual Conference, San Diego, CA, May 2000.

Makristathis et al., "Detection of Helicobacter pylori in Stool Specimens by PCR and Antigen Enzyme Immunoassay," *Journal of Clinical Microbiology*, vol. 36, No. 9, pp. 2772-2774, Sep. 1998.

\* cited by examiner

200bp amplifications
33 Cycles

| Lane | Q# | Sample Type | Sample Number | Grade |
|---|---|---|---|---|
| 1 | 7903.8 | Abnormal | 1 | A |
| 2 | 5627.4 | Abnormal | 2 | A |
| 3 | 8809.11 | Abnormal | 3 | A |
| 4 | 5421.94 | Abnormal | 4 | A |
| 5 | 1838.07 | Positive Control | | B |
| 6 | -549.23 | Normal | 5 | C |
| 7 | -715 | Normal | 6 | C |
| 8 | -1605.13 | Normal | 7 | C |
| 9 | -824.73 | Normal | 8 | C |
| 10 | 259.77 | Normal | 9 | C |
| 11 | | Neg Control | - | |
| 12 | | Neg Control | - | |
| 13 | 400 | 400 | Standard | |
| 14 | 2000 | 2000 | Standard | |
| 15 | 4000 | 4000 | Standard | |
| 16 | 6000 | 6000 | Standard | |
| 17 | 8000 | 8000 | Standard | |
| 18 | 10000 | 10000 | Standard | |

A= >2000
B= 500-2000
C= <500

200bp amplifications
35 Cycles

| Lane | Q# | Sample Type | Sample Number | Grade |
|---|---|---|---|---|
| 1 | 10851.04 | Abnormal | 1 | A |
| 2 | 8862.34 | Abnormal | 2 | A |
| 3 | 9777.85 | Abnormal | 3 | A |
| 4 | 6874.28 | Abnormal | 4 | A |
| 5 | 2392.07 | Positive Control | | B |
| 6 | 3060.62 | Normal | 5 | B |
| 7 | 813.45 | Normal | 6 | C |
| 8 | -720.04 | Normal | 7 | C |
| 9 | -442.2 | Normal | 8 | C |
| 10 | 1353.86 | Normal | 9 | B |
| 11 | | Neg Control | - | |
| 12 | | Neg Control | - | |
| 13 | 400 | 400 | Standard | |
| 14 | 2000 | 2000 | Standard | |
| 15 | 4000 | 4000 | Standard | |
| 16 | 6000 | 6000 | Standard | |
| 17 | 8000 | 8000 | Standard | |
| 18 | 10000 | 10000 | Standard | |

A= >5000
B= 1000-5000
C= <1000

200bp amplifications
34 Cycles

| Lane | Q# | Sample Type | Sample Number | Grade |
|---|---|---|---|---|
| 1 | 8428.34 | Abnormal | 1 | A |
| 2 | 4917.31 | Abnormal | 2 | A |
| 3 | 7742.22 | Abnormal | 3 | A |
| 4 | 3049.85 | Abnormal | 4 | A |
| 5 | 409.5 | Positive Control |  | B |
| 6 | -682.75 | Normal | 5 | C |
| 7 | -781.09 | Normal | 6 | C |
| 8 | -1099.28 | Normal | 7 | C |
| 9 | -1015.39 | Normal | 8 | C |
| 10 | 359.74 | Normal | 9 | B |
| 11 |  | Neg Control | - |  |
| 12 |  | Neg Control | - |  |
| 13 | 400 | 400 | Standard |  |
| 14 | 2000 | 2000 | Standard |  |
| 15 | 4000 | 4000 | Standard |  |
| 16 | 6000 | 6000 | Standard |  |
| 17 | 8000 | 8000 | Standard |  |
| 18 | 10000 | 10000 | Standard |  |

A= >750
B= 250-750
C= <250

200bp amplifications
33 Cycles

| Lane | Q# | Sample Type | Sample Number | Grade |
|---|---|---|---|---|
| 1 | 7878.15 | Abnormal | 1 | A |
| 2 | 4079.09 | Abnormal | 2 | A |
| 3 | 7995.95 | Abnormal | 3 | A |
| 4 | 2600.3 | Abnormal | 4 | A |
| 5 | 1698.19 | Positive Control |  | B |
| 6 | -405.32 | Normal | 5 | C |
| 7 | -466.15 | Normal | 6 | C |
| 8 | -1046.47 | Normal | 7 | C |
| 9 | -764.83 | Normal | 8 | C |
| 10 | 105.05 | Normal | 9 | C |
| 11 |  | Neg Control | - |  |
| 12 |  | Neg Control | - |  |
| 13 | 400 | 400 | Standard |  |
| 14 | 2000 | 2000 | Standard |  |
| 15 | 4000 | 4000 | Standard |  |
| 16 | 6000 | 6000 | Standard |  |
| 17 | 8000 | 8000 | Standard |  |
| 18 | 10000 | 10000 | Standard |  |

A= >2000
B= 500-2000
C= <500

200bp amplifications
34 Cycles

| Lane | Q# | Sample Type | Sample Number | Grade |
|------|------|---------------|---------------|-------|
| 1 | 7852.95 | Abnormal | 1 | A |
| 2 | 4797.07 | Abnormal | 2 | A |
| 3 | 8543.47 | Abnormal | 3 | A |
| 4 | 3597.23 | Abnormal | 4 | A |
| 5 | 943.64 | Positive Control | | B |
| 6 | -296.7 | Normal | 5 | C |
| 7 | -5.48 | Normal | 6 | C |
| 8 | -896.94 | Normal | 7 | C |
| 9 | -196.87 | Normal | 8 | C |
| 10 | 414.81 | Normal | 9 | C |
| 11 | | Neg Control | - | |
| 12 | | Neg Control | - | |
| 13 | 400 | 400 | Standard | |
| 14 | 2000 | 2000 | Standard | |
| 15 | 4000 | 4000 | Standard | |
| 16 | 6000 | 6000 | Standard | |
| 17 | 8000 | 8000 | Standard | |
| 18 | 10000 | 10000 | Standard | |

A= >2000
B= 500-2000
C= <500

200bp amplifications
34 Cycles

| Lane | Q# | Sample Type | Sample Number | Grade |
|---|---|---|---|---|
| 1 | 7660.6 | Abnormal | 1 | A |
| 2 | 7032.89 | Abnormal | 2 | A |
| 3 | 8364.31 | Abnormal | 3 | A |
| 4 | 6892.04 | Abnormal | 4 | A |
| 5 | 4883.47 | Positive Control | | A |
| 6 | 1934.67 | Normal | 5 | B |
| 7 | 1380.84 | Normal | 6 | B |
| 8 | -964.17 | Normal | 7 | C |
| 9 | 1729.51 | Normal | 8 | B |
| 10 | 2221.69 | Normal | 9 | B |
| 11 | | Neg Control | - | |
| 12 | | Neg Control | - | |
| 13 | 400 | 400 | Standard | |
| 14 | 2000 | 2000 | Standard | |
| 15 | 4000 | 4000 | Standard | |
| 16 | 6000 | 6000 | Standard | |
| 17 | 8000 | 8000 | Standard | |
| 18 | 10000 | 10000 | Standard | |

A= >5000
B= 1000-5000
C= <1000

200bp amplifications
33 Cycles

| Lane | Q# | Sample Type | Sample Number | Grade |
|------|---------|----------------|---------------|-------|
| 1 | 6519.13 | Abnormal | 1 | A |
| 2 | 5745.19 | Abnormal | 2 | A |
| 3 | 9765.65 | Abnormal | 3 | A |
| 4 | 4153.79 | Abnormal | 4 | A |
| 5 | 1869.33 | Positive Control | | B |
| 6 | 418.37 | Normal | 5 | C |
| 7 | 405.91 | Normal | 6 | C |
| 8 | -258.08 | Normal | 7 | C |
| 9 | 141.64 | Normal | 8 | C |
| 10 | 450.78 | Normal | 9 | C |
| 11 | | Neg Control | - | |
| 12 | | Neg Control | - | |
| 13 | 400 | 400 | Standard | |
| 14 | 2000 | 2000 | Standard | |
| 15 | 4000 | 4000 | Standard | |
| 16 | 6000 | 6000 | Standard | |
| 17 | 8000 | 8000 | Standard | |
| 18 | 10000 | 10000 | Standard | |

A= >2000
B= 500-2000
C= <500

1.8 kb amplifications
36 Cycles

| Lane | Q# | Sample |
|------|---------|-------------|
| 1 | | Neg Control |
| 2 | 102.935 | Abnormal |
| 3 | 260.645 | Abnormal |
| 4 | 0.075 | Normal |
| 5 | 48.305 | Abnormal |
| 6 | 0.045 | Normal |
| 7 | 18.575 | Normal |
| 8 | | Neg Control |
| 9 | | Neg Control |
| 10 | 75 | 75 |
| 11 | 125 | 125 |
| 12 | 250 | 250 |
| 13 | 500 | 500 |
| 14 | 1000 | 1000 |

Abnormal / Normal cutoff     40

1.8 kb amplifications
38 Cycles

| Lane | Q# | Sample |
|---|---|---|
| 1 | | Neg Control |
| 2 | 81.84 | Abnormal |
| 3 | 91.515 | Abnormal |
| 4 | 0.04 | Normal |
| 5 | 24.86 | Abnormal |
| 6 | 0.88 | Normal |
| 7 | 17.25 | Normal |
| 8 | | Neg Control |
| 9 | | Neg Control |
| 10 | 75 | 75 |
| 11 | 125 | 125 |
| 12 | 250 | 250 |
| 13 | 500 | 500 |
| 14 | 1000 | 1000 |

Abnormal / Normal cutoff    20

1.8 kb amplifications
40 Cycles

| Lane | Q# | Sample |
|---|---|---|
| 1 | | Neg Control |
| 2 | 70.72 | Abnormal |
| 3 | 92.78 | Abnormal |
| 4 | 96.76 | Abnormal |
| 5 | 0.00 | Normal |
| 6 | 29.85 | Abnormal |
| 7 | 0.00 | Normal |
| 8 | 2.00 | Normal |
| 9 | | Neg Control |
| 10 | | Neg Control |
| 11 | 75 | 75 |
| 12 | 125 | 125 |
| 13 | 250 | 250 |
| 14 | 500 | 500 |
| 15 | 1000 | 1000 |
| 16 | 2000 | 2000 |

Abnormal / Normal cutoff     10

FIGURE 11A

Gel #1

| Lane # | Clinical Status | Results |
|---|---|---|
| A | Marker Lane | |
| N | Negative Control | |
| N | Negative Control | |
| 1 | Cancer | |
| 2 | Normal | |
| 3 | Cancer | |
| 4 | Normal | |
| 5 | Normal | |
| 6 | Normal | |
| 7 | Normal | |
| 8 | Normal | |
| 9 | Normal | |
| 10 | Normal | |
| 11 | Cancer | |
| 12 | Normal | |
| 13 | Normal | |
| 14 | Normal | |
| 15 | Normal | |
| N | Negative Control | |
| NA | Standard Curve | |
| NA | Standard Curve | |
| NA | Standard Curve | |
| NA | Standard Curve | |
| NA | Standard Curve | |
| B | Markers | |

|  | Gel #2 | Results |
|---|---|---|
| A | Markers | |
| N | Negative Control | |
| N | Negative Control | |
| 16 | Normal | |
| 17 | Normal | |
| 18 | Cancer | |
| 19 | Normal | |
| 20 | Normal | |
| 21 | Normal | |
| 22 | Normal | |
| 23 | Normal | |
| 24 | Normal | |
| 25 | Normal | |
| 26 | Normal | |
| 27 | Normal | |
| 28 | Normal | |
| 29 | Normal | |
| 30 | Normal | |
| N | Negative Control | |
| NA | Standard Curve | |
| NA | Standard Curve | |
| NA | Standard Curve | |
| NA | Standard Curve | |
| NA | Standard Curve | |
| B | Markers | |

FIGURE 11B

METHODS OF SCREENING FOR SUPRACOLONIC NEOPLASMS BASED ON STOOL SAMPLES CONTAINING A NUCLEIC ACID MARKER INDICATIVE OF A NEOPLASM

CROSS-REFERENCE TO RELATED APPLICATIONS

This application is a continuation of U.S. Ser. No. 10/149,464, filed Mar. 18, 2003, U.S. Pat. No. 7,368,233, which is the national phase of International (PCT) Patent Application Serial No. PCT/US00/42683, filed Dec. 7, 2000, published under PCT Article 21(2) in English, which claims priority to and the benefit of U.S. Provisional Application Ser. Nos. 60/169,457, filed Dec. 7, 1999, and 60/196,074, filed Apr. 10, 2000. The disclosures of all of these applications are incorporated herein by reference.

STATEMENT AS TO FEDERALLY SPONSORED RESEARCH

This invention was made with government support under CA071680 awarded by the National Cancer Institute. The government has certain rights in the invention.

FIELD OF THE INVENTION

The invention relates to methods and materials involved in the detection of supracolonic aerodigestive premalignant and malignant neoplasms.

BACKGROUND

About half of all cancer deaths in the United States result from aerodigestive cancer. For example, of the estimated 564,800 annual cancer deaths, 160,100 (25%) result from lung cancer; 56,500 (10%) result from colorectal cancer; 28,900 (6%) result from pancreas cancer; 13,700 (3%) result from stomach cancer; and 11,900 (3%) result from esophagus cancer. In addition, over 7 percent of the annual cancer deaths result from other aerodigestive cancers such as naso-oropharyngeal, bile duct, gall bladder, and small bowel cancers (Landis et al., *CA Cancer J. Clin.*, 48:6-29 (1998)).

Attempts have been made to identify and use nucleic acid markers that are indicative of cancer. For example, mutations in the p53 cell cycle regulator gene have been associated with numerous cancers, especially colorectal cancer, and it has been suggested that specific mutations might be a basis for molecular screening assays for the early stages of certain types of cancer. See, e.g., Sidransky, et al., *Science*, 256: 102-105 (1992).

SUMMARY OF THE INVENTION

The invention involves detecting premalignant and malignant supracolonic aerodigestive neoplasms. According to the invention, a supracolonic aerodigestive neoplasm is a neoplasm in an aerodigestive tissue proximal to (above) the colon. An aerodigestive tissue is a tissue characterized by a lumenal space that is connected to the lumenal spaces of the respiratory and digestive tracts. Supracolonic aerodigestive tissue includes tissue such as a mammal's small intestine, gall bladder, bile duct, pancreas, liver, stomach, esophagus, lung, and naso-oro-pharyngeal airways. Supracolonic aerodigestive tissue does not include tissue such as blood, serum, bone, connective tissue or other tissue that is not directly connected to a lumen of the aerodigestive tract.

The invention involves determining whether a stool sample from a mammal contains a neoplasm-specific marker from a supracolonic aerodigestive neoplasm. The detection of a neoplasm-specific marker in a mammal's stool allows a physician to screen for a supracolonic aerodigestive neoplasm much earlier than currently available cancer detection techniques. In addition, the analysis of a stool sample is much less invasive than other types of diagnostic techniques such as endoscopy.

The invention is based on the discovery that neoplasm-specific markers from a neoplasm located in an aerodigestive tissue proximal to the colon (e.g., in the small intestine, gall bladder, bile duct, pancreas, liver, stomach, esophagus, lung, and naso-oro-pharyngeal airways) can be detected in that mammal's stool. Thus, stool can be analyzed to identify mammals having cancer other than colorectal cancer. Once a particular patient is determined to have stool containing a neoplasm-specific marker, additional cancer screening techniques can be used to identify the exact location and nature of the neoplasm. For example, a stool sample can be analyzed to determine that the patient has a neoplasm, while magnetic resonance imaging (MRI), endoscopic analysis (e.g., colonoscopy, gastroscopy, and bronchoscopy), and tissue biopsy techniques can be used to identify the exact location and nature of the neoplasm in the supracolonic aerodigestive tract. Thus, the invention provides convenient methods that can be used to screen and identify patients having a supracolonic aerodigestive neoplasm.

In general, one aspect of the invention features a method for detecting a lung neoplasm in a mammal, preferably a human. The method includes determining whether a stool sample from the mammal contains a neoplasm-specific marker associated with lung cancer. The lung neoplasm can include a premalignant neoplasm or malignant neoplasm. The neoplasm-specific marker can include a neoplasm-specific nucleic acid marker. The neoplasm-specific nucleic acid marker can include a nucleic acid having a point mutation. The point mutation can be located in a K-ras, APC, or p53 gene. The neoplasm-specific nucleic acid marker can include nucleic acid that reflects microsatellite instability. The microsatellite instability can be located in the BAT-26 segment of the MSH2 mismatch repair gene. The neoplasm-specific nucleic acid marker can include long DNA (e.g., DNA greater than about 270, 300, 400, 500, 600, 700, 800, 900, 1000, 1500, 2000, or 2500 base pairs in length). The neoplasm-specific marker can include a neoplasm-specific polypeptide marker or a neoplasm-specific cell marker. A method of the invention can include determining whether the stool sample contains two or more neoplasm-specific markers. The two or more neoplasm-specific markers can be nucleic acid markers, polypeptide markers, and/or cell markers. For example, the two or more neoplasm-specific markers can be neoplasm-specific nucleic acid markers, and the two or more neoplasm-specific nucleic acid markers can include nucleic acid having a point mutation, nucleic acid that reflects microsatellite instability, and/or long DNA.

In another aspect, the invention features a method for detecting a naso-oro-pharyngeal neoplasm in a mammal. The method includes determining whether a stool sample from the mammal contains a neoplasm-specific marker, where the marker is from the naso-oro-pharyngeal neoplasm.

Another aspect of the invention features a method for detecting an esophageal neoplasm in a mammal. The method includes determining whether a stool sample from the mammal contains a neoplasm-specific marker, where the marker is from the esophageal neoplasm.

Another aspect of the invention features a method for detecting a stomach neoplasm in a mammal. The method includes determining whether a stool sample from the mammal contains a neoplasm-specific marker, where the marker is from the stomach neoplasm.

Another aspect of the invention features a method for detecting a liver neoplasm in a mammal. The method includes determining whether a stool sample from the mammal contains a neoplasm-specific marker, where the marker is from the liver neoplasm.

Another aspect of the invention features a method for detecting a bile duct neoplasm in a mammal. The method includes determining whether a stool sample from the mammal contains a neoplasm-specific marker, where the marker is from the bile duct neoplasm.

Another aspect of the invention features a method for detecting a gall bladder neoplasm in a mammal. The method includes determining whether a stool sample from the mammal contains a neoplasm-specific marker, where the marker is from the gall bladder neoplasm.

Another aspect of the invention features a method for detecting a small intestine neoplasm (e.g., duodenum, jejunum, and/or ileum neoplasm) in a mammal. The method includes determining whether a stool sample from the mammal contains a neoplasm-specific nucleic acid marker, where the marker is from the small intestine neoplasm.

Another aspect of the invention features a method for detecting a pancreatic neoplasm in a mammal. The method includes determining whether a stool sample from the mammal contains long DNA, where the long DNA is from the pancreatic neoplasm. Another aspect of the invention features a method for detecting a pancreas neoplasm in a mammal, including determining whether a stool sample from the mammal contains two or more neoplasm-specific markers, where the markers are from the pancreas neoplasm.

In another embodiment of the invention, the nucleic acid being analyzed is selected from a coding region of a gene, or portion thereof, a noncoding nucleic acid region, or portion thereof, a regulatory element of a gene or a portion thereof, and an unidentified fragment of genomic DNA.

Methods of the invention are useful as diagnostic screening methods. Often it is desirable to perform follow-up testing on a patient in order to confirm a suspected disease location in the aerodigestive tract. Such follow-up procedures are determined based upon the disease state being interrogated. For example, a colonoscopy, gastroscopy, or bronchoscopy may be suggested in a case in which a stool sample is positively screened according to methods of the invention. Such follow-up procedures are contemplated herein as part of the invention.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects and advantages of the invention are apparent upon consideration of the following detailed description, drawings and claims.

DESCRIPTION OF THE DRAWINGS

FIGS. 11A and B are gel photographs of results of amplification of DNA in stool from a total of 30 patients and controls. The band intensity relates to the amount of amplifiable DNA in the sample. Lanes N are negative controls, lanes 1, 3, 11, and 18 are results from patients which are indicative of the presence of cancer or adenoma, lanes 2, 4, 5-10, 12-17, and 19-30 are results from patients which are indicative of the absence of cancer or adenoma. The remaining lanes are markers or standards.

Figure 1:
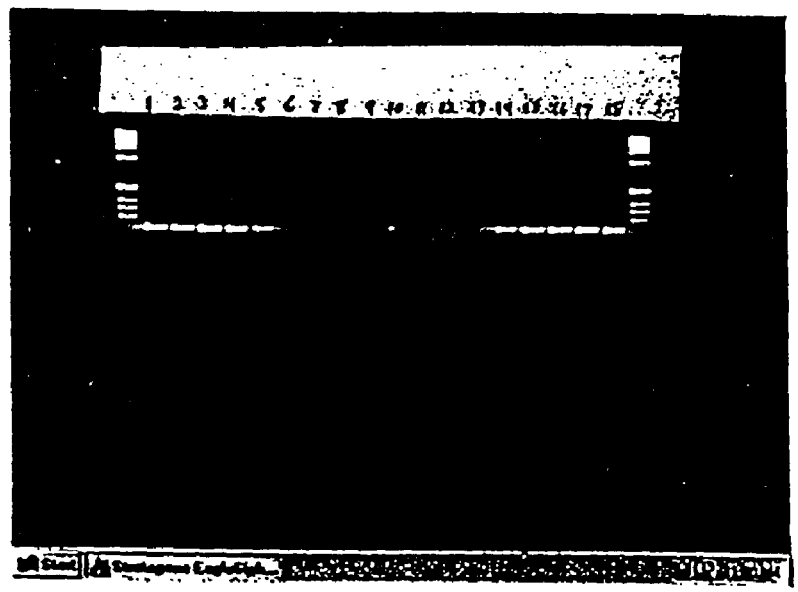
FIG. 1 is a gel photograph showing results of amplification of K-ras (exon 1) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure.
Figure 2:
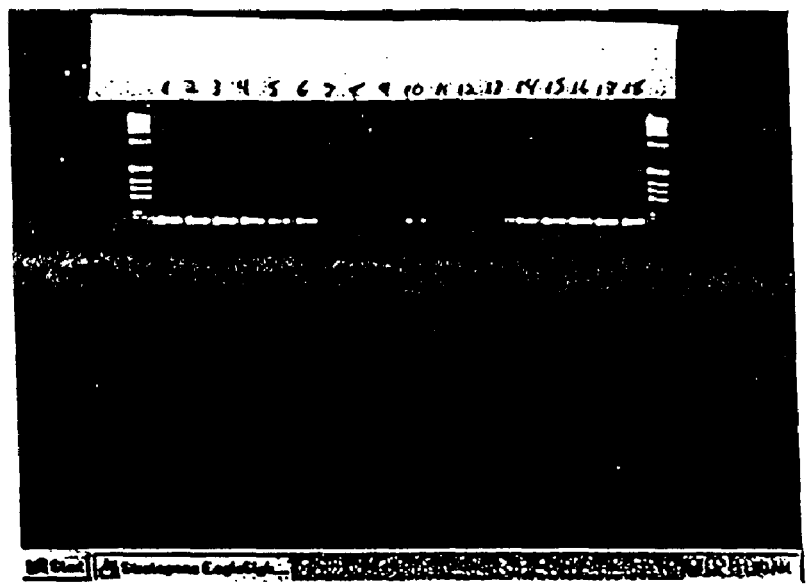
FIGS. 2-4 are gel photographs showing results of amplification of apc (exon 15) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure.
Figure 3:
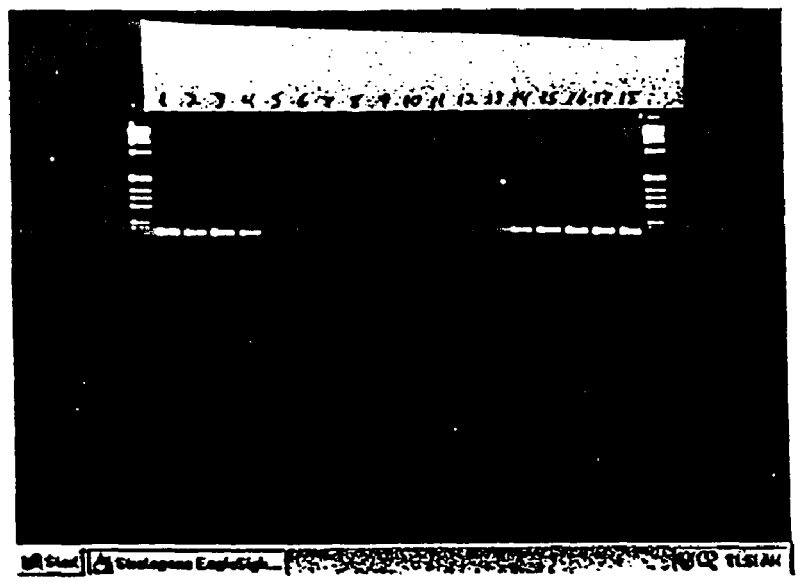
Figure 4:
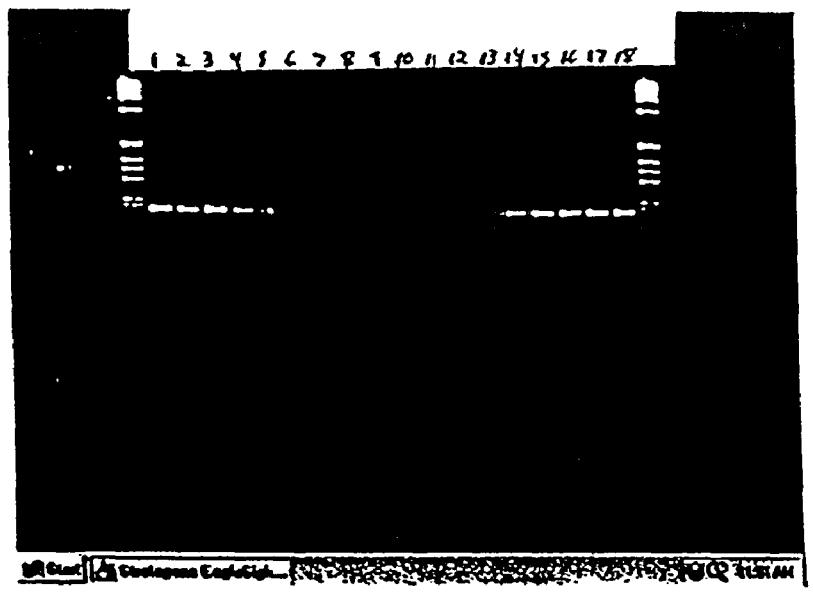
Figure 5:
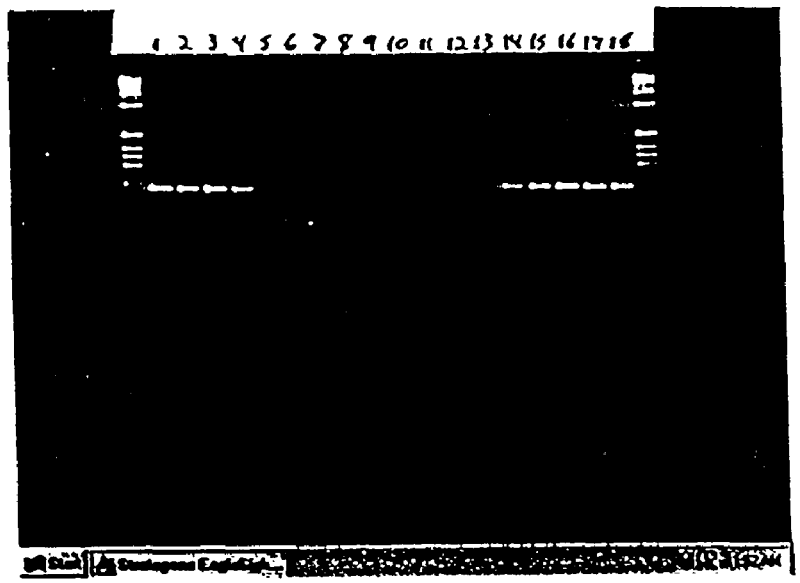
FIG. 5 is a gel photograph showing results of amplification of p53 (exon 5) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure.
Figure 6:
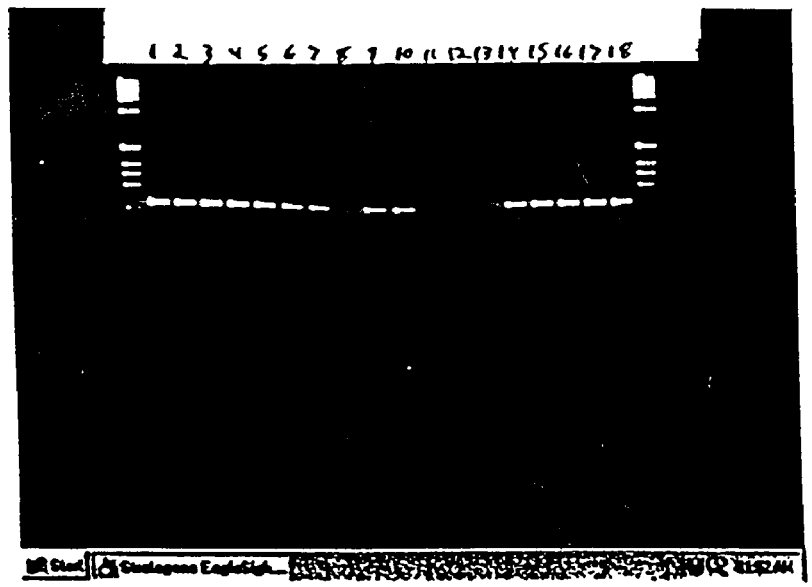
FIG. 6 is a gel photograph showing results of amplification of p53 (exon 7) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure.
Figure 7:
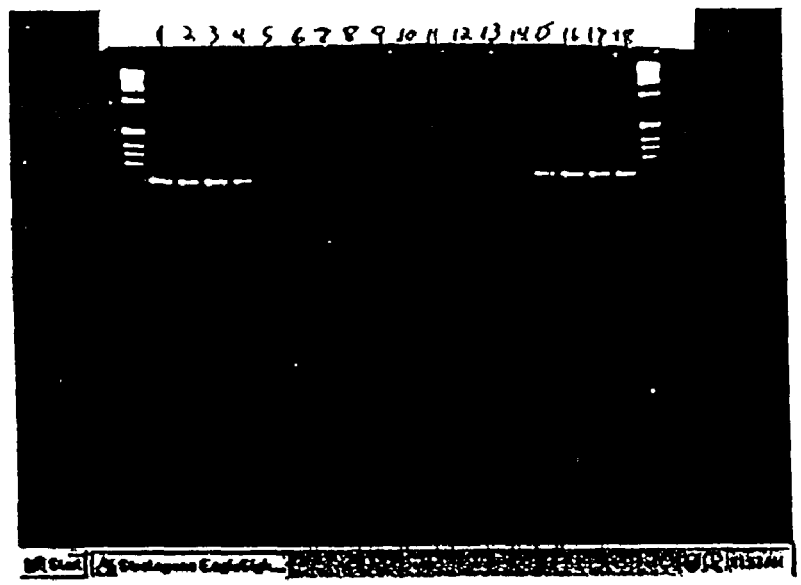
FIG. 7 is a gel photograph showing results of amplification of p53 (exon 8) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure.

The amplification reactions described above may be conducted according to any suitable or convenient protocol and the fragment size of the resulting amplification products (if any) may be determined by any suitable or convenient means.

DETAILED DESCRIPTION

The invention provides methods and materials related to the detection of neoplasm-specific markers from the aerodigestive tract in a stool sample. Specifically, the invention provides methods and materials for identifying mammals having a supracolonic aerodigestive neoplasm by detecting a neoplasm-specific marker in a stool sample obtained from the mammal. For example, the invention provides methods for detecting a neoplasm in the small intestine, gall bladder, bile duct, pancreas, liver, stomach, esophagus, lung, or naso-oropharyngeal neoplasm of a mammal. A small intestine neoplasm can be a duodenum, jejunum, or ileum neoplasm. It will be appreciated that the methods and materials of the invention can be used to detect a neoplasm-specific marker in a mammal having a combination of different supracolonic aerodigestive neoplasms. For example, the methods and materials of the invention can be used to detect a neoplasm-specific marker in a human having a lung and stomach neoplasm. The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

While not being limited to any particular mode of action, the invention appears to be based on the fact that premalignant and malignant neoplasms arising in a mammal's small intestine, gull bladder, bile duct, pancreas, liver, stomach, esophagus, lung, ornaso-oro-naso-oro-pharyngeal airways can shed cells into the aerodigestive lumen. These exfoliated cells as well as their constituents can survive transit through the gastrointestinal tract and ultimately pass as fecal waste. For example, as described herein, a neoplasm-specific marker can be detected in a stool sample collected from a human having lung cancer. In this case, cancer cells and their constituents leave the lung, enter the digestive tract, and exit the body as fecal waste.

Nucleic Acid Markers

Neoplasm-specific markers can be nucleic acid. Examples of neoplasm-specific nucleic acid markers include, without limitation, nucleic acid having a point mutation, nucleic acid that reflects microsatellite instability, and long DNA. Nucleic acid having a point mutation can encode a polypeptide or regulate the expression of a polypeptide (e.g., promoters, enhancers, and silencers). Examples of nucleic acid that can contain a point mutation indicative of a neoplasm include, without limitation, the genes for K-ras, APC (adenomatous polyposis coli), and p53.

Nucleic acid that reflects microsatellite instability can be used to indicate the presence of a neoplasm. Briefly, nucleic acid that reflects microsatellite instability can be identified as described elsewhere (Samowitz et al., *Am. J. Path.*, 154:1637-1641 (1999) and Hoang et al., *Cancer Res.*, 57:300-303 (1997)). An example of nucleic acid that can reflect microsatellite instability indicative of a neoplasm includes, without limitation, the gene for BAT-26.

While each type of supracolonic aerodigestive neoplasm (e.g., lung, stomach, etc.) is associated with some DNA alterations unique to the site, many of the mutations commonly present involve the same genes as those found in colorectal neoplasia—especially with respect to mutations on K-ras, APC, and p53 as well as to microsatellite instability (Table I).

TABLE I

Proportion of different gene mutations found in different supracolonic aerodigestivetissue neoplasms.

| | K-ras | APC | P53 | MSI |
|---|---|---|---|---|
| Lung | >30% | 30-80% | >50% | 30-66% |
| Esophagus | Low | >30% | >50% | >50% |
| Stomach | Low | 50-80% | >50% | >30% |
| Bile Duct | 17-60% | | 20-67% | |

Long DNA is a marker for non-apoptotic cells. Typically, cells shed from normal mucosa are apoptotic, while those shed from colorectal and supracolonic aerodigestive neoplasms are non-apoptotic. As described herein, long DNA can be used as a neoplasm-specific marker for patients having a supracolonic aerodigestive neoplasm such as a small intestine, gall bladder, bile duct, pancreas, liver, stomach, esophagus, lung, or naso-oro-pharyngeal neoplasm. One hallmark of apoptosis is the autodigestion or cleavage of DNA into "short" fragments of about 180 base-pairs. The detection of "long" DNA (i.e., DNA greater than about 200 base-pairs) in a stool sample can indicate the presence of non-apoptotic cells of neoplastic lineage derived from a supracolonic aerodigestive neoplasm. The term "long DNA" as used herein refers to DNA greater than about 200 base-pairs (e.g., greater than about 250, 300, 350, 400, 500, 600, 700, 800, 900, 1000, 1250, 1500, 1750, 2000, or 2500 base-pairs).

Any method can be used to detect a neoplasm-specific nucleic acid marker in a stool sample. For example, once a stool sample is collected and the mammal's nucleic acid isolated, PCR can be used to detect the presence or absence of particular nucleic acid markers such as a nucleic acid having a particular point mutation, a nucleic acid that reflects microsatellite instability, and long DNA. It is noted that a single stool sample can be analyzed for one neoplasm-specific marker or for multiple neoplasm-specific markers. For example, a stool sample can be analyzed using assays that detect a panel of different neoplasm-specific markers. In addition, multiple stool samples can be collected for a single mammal and analyzed as described herein. U.S. Pat. Nos. 5,670,325; 5,741,650; 5,928,870; 5,952,178; and 6,020,137 describe various methods that can be used to prepare and analyze stool samples.

Polypeptide Markers

Neoplasm-specific markers can be polypeptides. Examples of neoplasm-specific polypeptide markers include, without limitation, oncogenic polypeptides and mutated polypeptides. Examples of polypeptides that can be indicative of a neoplasm include, without limitation, K-ras, APC, and p53. Any method can be used to detect a neoplasm-specific polypeptide marker. For example, antibodies specific for the polypeptide marker can be used in an immunoassay (e.g., ELISA) to detect the presence or absence of the polypeptide in a stool sample that is indicative of the presence of an aerodigestive neoplasm.

Cell and Cell Component Markers

Neoplasm-specific markers can be cells or cell components (i.e., cell markers). Examples of neoplasm-specific cell or cell component markers include, without limitation, tumor cells and tumor cell components (e.g., cell membranes). U.S. Pat.

No. 5,891,651 describes methods and materials that can be used to detect neoplasm-specific cell or cell component markers in stool samples.

The invention will be further described in the following examples, which do not limit the scope of the invention described in the claims.

EXAMPLES

Example 1

The Three Component Test

The three component test can detect three different types of neoplasm-specific nucleic acid markers from supracolonic aerodigestive neoplasm: (1) nucleic acid having a point mutation, (2) nucleic acid that reflects microsatellite instability, and (3) long DNA. Briefly, stool samples were thawed at room temperature and homogenized in an excess volume (>1:10 w:v) of EXACT buffer A (EXACT Laboratories, Maynard, Mass.) utilizing an EXACTOR stool shaker (EXACT Laboratories Maynard, Mass.). Following homogenization, a four gram stool equivalent of each sample was centrifuged to remove all particulate matter, and the supernatants incubated at 37° C. following addition of Proteinase K (0.5 μg/μL) and SDS (0.5%). The supernatants were subsequently extracted with Tris saturated phenol (Gibco/BRL, Grand Island, N.Y.), phenol/chloroform/isoamyl alcohol (25:24:1), and chloroform. Total nucleic acid was then precipitated (1/10 volume 3M NaAc and an equal volume isopropanol), removed from solution by centrifugation, and resuspended in TE (0.01M Tris pH 7.4, 0.001M EDTA) buffer containing RNase A (2.5 μg/mL). For each group of samples prepared, process positive control samples as well as component negative controls were included.

Sequence specific DNA fragments were purified from the total nucleic acid preparations by performing oligonucleotide-based hybrid capture. For each sample, seven hybrid capture reactions were performed in duplicate. Each capture reaction was carried out by adding 300 μL of sample preparation to an equal volume of 6M Guanidine Isothiocyanate solution (Gibco/BRL, Grand Island, N.Y.)) containing biotinylated sequence specific oligonucleotides (20 pmoles) (Midland Certified Reagent Co., Midland, Tex.). The sequence of each oligonucleotide was specific for the DNA fragment to be analyzed. For example, an oligonucleotide having specificity for a region of the K-ras gene was used to capture a fragment that could contain the K-ras mutations. Following a two-hour incubation at 25° C., strepavidin coated magnetic beads were added to the solution, and the tubes were incubated for an additional hour at room temperature. The bead/hybrid capture complexes were then washed four times with 1×B+W buffer (1 M NaCl, 0.01 M Tris-HCl pH 7.2, 0.001M EDTA 0.1% Tween 20), and the sequence specific captured DNA was eluted into 35 μL L-TE (1 mM Tris pH 7.4, 0.1M EDTA) by heat denaturation.

PCR amplifications (50 μL) were performed on MJ Research Tetrad Cyclers (Watertown, Mass.) using 10 μL of captured DNA, 1× GeneAmp PCR buffer (PE Biosystems, Foster City, Calif.), 0.2 mM dNTPs (Promega, Madison, Wis.), 0.5 μM sequence specific primers (Midland Certified Reagent Co., Midland, Tex.) and 5 units Amplitaq DNA polymerase (PE Applied Biosystems, Norwalk, Conn.). All of the sequence specific amplification reactions were carried out under identical thermocycler conditions. Following an initial denaturation of 94° C. for 5 min, PCR amplification was performed for 40 cycles consisting of 1 min at 94° C., 1 min at 60° C., and 1 min at 72° C., with a final extension of 5 min at 72° C. For PCR product analysis, 8 μL of each amplification reaction was loaded and electrophoresed on a 4% ethidium bromide-stained NuSieve 3:1 agarose gels (FMC, Rockland, Me.) and visualized with a Stratagene EagleEye II (Stratagene, La Jolla, Calif.) still image system.

The presence or absence of point mutations or BAT-26 associated mutations was determined by using a modified solid phase minisequencing method (Syvanen et al., *Genomics*, 8:684-692 (1990)). Point mutation targets included codons K12p1, K12p2, and K13p2 of the K-ras gene; codons 1309 delta 5, 1367p1, 1378p1, and 1450p1 of the APC gene; and codons 175p2, 245p1, 245p2, 248p1, 248p2, 273p1, 273p2, and 282p1 of the p53 gene. For all gene targets, both wild-type and mutant specific reactions were performed. Within the wild-type reactions, radionucleotide bases complementary to the wild-type base were added. For each point mutation specific reaction, radionucleotide bases complementary to the expected mutant bases were added in addition to unlabeled dideoxy nucleotides complementary to the wild-type base. BAT-26 mutations associated with a 4-15 bp deletion were identified by size discrimination of reaction products.

The presence of long DNA was determined by analyzing the relative intensity of each sample specific PCR product. For each stool sample analyzed, 7 unique PCR amplification products were generated in duplicate (or 14 amplifications per subject) and independently scored by two technicians. PCR product intensities were scored as high, medium, or low by visual examination of the gel image (Grades A, B, and C, respectively).

Examples 2-4

Experiments were conducted to determine whether the presence of long DNA in stool were predictive of supracolonic aerodigestive neoplasm in patients from whom stools samples were obtained. In the first experiment (Example 2), the amount of amplifiable DNA was measured in each of several stool samples using PCR amplification to detect DNA fragments in the sample of at least 200 base pairs in length. The second experiment (Example 3) determined the amount of long fragments (greater than 200 base pair) in the same samples, and then determined ratios of long product to short product. The third experiment (Example 4) determined a profile of amplification products with nucleic acid fragment lengths of 200 bp, 400 bp, 800 bp, 1.3 Kb, 1.8 Kb and 2.4 Kb.

The size of human DNA fragments obtained above can be determined by numerous means. For example, human DNA can be separated using gel electrophoresis. A 3% agarose gel is prepared using techniques known in the art. See Ausubel et. al., Short Protocols in Molecular Biology, John Wiley & Sones, 1195, pgs. 2-23-2-24, incorporated by reference herein. The size of human DNA fragments is then determined by comparison to known standards. Fragments greater than about 200 bp provide a positive screen.

Example 2

Stool samples were collected from 9 patients who presented with symptoms or a medical history that indicated that a colonoscopy should be performed. Each stool sample was frozen. Immediately after providing a stool sample, each patient was given a colonoscopy in order to determine the patient's disease status. Based upon the colonoscopy results, and subsequent histological analysis of biopsy samples taken during colonoscopy, individuals were placed into one of two groups: normal or abnormal. The abnormal group consisted of patients with colorectal cancer or with an adenoma of at least 1 cm in diameter. Based upon these results, 4 of the 9 patients were placed into the abnormal group.

The samples were screened by determining the amount of amplifiable DNA having at least 200 base pairs.

Human DNA was isolated and amplified using PCR. Each sample was amplified using forward and reverse primers through 7 loci (Kras, exon 1, APC exon 15 (3 separate loci), p53, exon 5, p53, exon 7, and p53, exon 8) in duplicate (for a total of 14 amplifications for each locus). Seven separate PCRs (40 cycles each) were run in duplicate using primers directed to detect fragments in the sample having 200 base pairs or more. Amplified DNA was placed on a 4% Nusieve (FMC Biochemical) gel (3% Nusieve, 1% agarose), and stained with ethidium bromide (0.5 µg/ml). The resulting amplified DNA was graded based upon the relative intensity of the stained gels. The results are shown in FIGS. 1-7. Each Figure represents the results for all 9 patients (including standards) for the seven different loci that were amplified. As shown in the Figures, each sample from a patient with colorectal cancer or adenoma was detected as a band having significantly greater intensity than the bands associated with samples from patients who did not have colorectal cancer or precancer. All four colorectal cancer/adenoma patients identified using colonoscopy were correctly identified by determining the amount of amplifiable DNA 200 base pairs or greater in length. As shown in FIGS. 1-7, the results were the same regardless of which locus was amplified. Accordingly, the amount of 200 bp or greater DNA in a sample was predictive of patient disease status.

Example 3

An experiment was conducted that was essentially identical to the one described above in Example 2, but forward and reverse primers were placed such that fragments of about 1.8 Kb and above were amplified.

Figure 8:
FIGS. 8-10 are gel photographs of results of amplification of DNA from stool samples using forward and reverse primers spaced approximately 1.8 Kb apart. The band intensity shows the amount of 1.8 Kb or greater product. Lanes 1, 8, and 9 are negative controls, lanes 2, 3, and 5 are results from patients with cancer or adenoma, lanes 4, 6, and 7 are results from patients who did not have cancer or adenoma, and lanes 10-14 are molecular weight standards.
Figure 9:
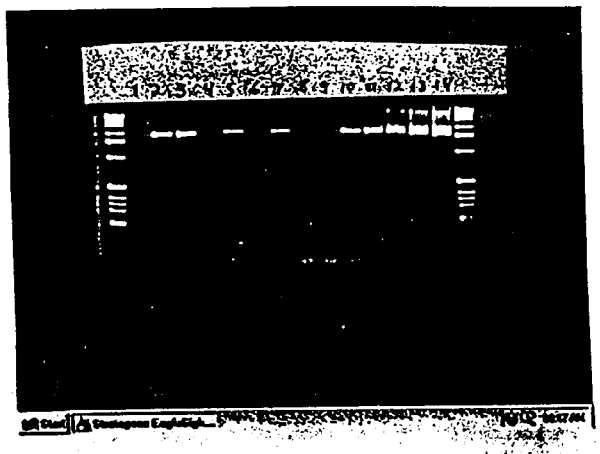
Figure 10:
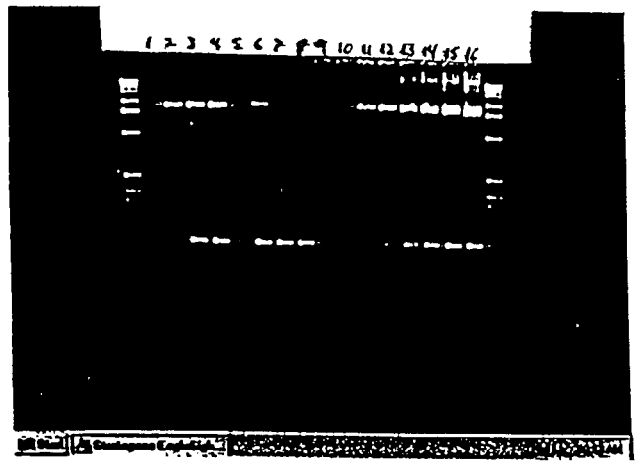
Figure 12:
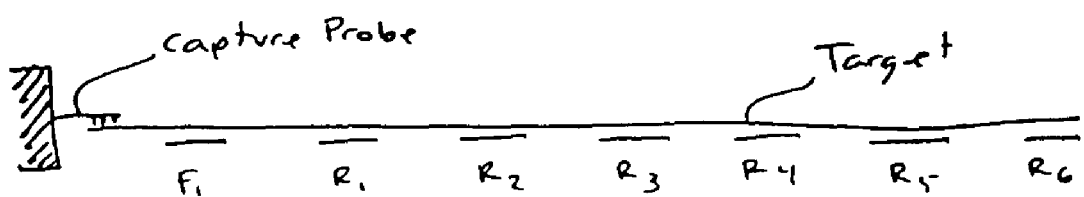
FIGS. 12-13 illustrate embodiments of target nucleic acid captured by a capture probe and different configurations of forward (F) and reverse (R) primers.
Figure 13:
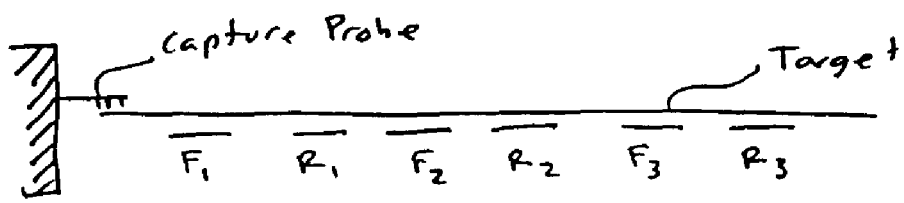

Forward and reverse primers were spaced so as to hybridize approximately 1.8 Kb apart on three different loci (Kras, exon 1, APC exon 15, and p53 exon 5). Thirty-three rounds of amplification were performed, and the resulting DNA was placed on a 3% agarose gel. The results are shown in FIGS. 8-10. As shown in the Figures (which show results from three separate experiments to amplify and detect "long" product), samples from individuals having colorectal cancer or precancer produced large amounts of long (in this case 1.8 Kb and above) DNA; whereas samples from patients who did not have cancer or precancer produced no DNA in the range of about 1.8 Kb and higher. Thus, the presence of long DNA was indicative of the disease status of the patient.

Example 4

An experiment was conducted to determine the molecular weight profile of DNA from samples collected and prepared as part of a blind study on 30 patients who presented at the Mayo Clinic with suspected gastrointestinal disorders. Stool samples were obtained, and DNA was isolated as described above.

According to methods of the invention, amplification reactions were conducted using forward and reverse primers through the 5 loci for each sample. Forward and reverse primers were spaced to amplify fragments of 200 bp, 400 bp, 800 bp, 1.3 Kb, 1.8 Kb, and 2.4 Kb. Each of 30 PCR reactions was run for 36 cycles. Amplicon was run on a 3% Seakeam gel, and stained with ethidium bromide. The results are shown in FIGS. 11A and 11B. Each figure represents the results for 15 of the 30 patients.

As shown in those figures, patients with cancer or adenoma have an increased yield of long DNA. That is especially true at the 1.8 Kb level and above. Thus, patients with cancer or adenoma produce larger DNA fragments than are produced in the stool of patients who do not have cancer. Thus, the presence of high molecular weight DNA, especially that at 1.8 Kb and above, were indicative of the presence of cancer.

Example 5

In this example, methods of the invention were correlated with clinical outcome in numerous patients who had a colorectal adenoma or colorectal cancer as diagnosed using colonoscopy, and 79 patients who were diagnosed as not having colorectal cancer or adenoma. A stool sample was obtained from each of these patients and prepared as described above. Fragments of the 5 different loci referred to above were amplified using primers spaced 200, 400, 800, 1300, 1800, and 2400 base pairs apart using the protocol described above in Example 4. Each amplification was scored such that successful amplification of a fragment received a score of 1, and no amplification received a score of 0. Since five loci were interrogated using 6 primer pairs each, the maximum score was 30 (successful amplification of all 6 fragments at all five loci). The cutoff for a positive screen was set at 21. The results are shown below.

TABLE 1

| | Normals | |
|---|---|---|
| Patient No. | Age | Score |
| P-178 | 64 | 19 |
| P-185 | 50 | 18 |
| P-033 | 56 | 16 |
| P-177 | 67 | 14 |
| P-055 | 75 | 13 |
| P-029 | 70 | 12 |
| P-079 | 63 | 12 |
| P-066 | 72 | 11 |
| P-027 | 65 | 10 |
| P-054 | 72 | 9 |
| P-158 | 59 | 9 |
| P-043 | 56 | 8 |
| P-009 | 73 | 7 |
| P-030 | 86 | 2 |
| P-032 | 51 | 1 |
| P-068 | 58 | 1 |
| P-187 | 63 | 1 |
| P-018 | 68 | 0 |
| P-186 | 61 | 17 |
| P-135 | 67 | 14 |
| P-120 | 75 | 13 |
| P-179 | 76 | 9 |
| P-057 | 56 | 7 |
| P-143 | 65 | 6 |
| P-136 | 58 | 1 |
| P-012 | 75 | 0 |

TABLE 2

| | Adenomas | |
|---|---|---|
| Patient No. | Age | Score |
| P-003 | | 29 |
| P-001 | | 23 |
| P-045 | | 22 |

TABLE 2-continued

Adenomas

| Patient No. | Age | Score |
|---|---|---|
| P-162 | | 21 |
| P-163 | | 16 |
| P-088 | | 15 |
| P-050 | | 13 |
| P-060 | | 11 |
| P-061 | | 11 |
| P1058 | | 10 |
| P-075 | | 10 |
| P-077 | | 8 |
| P-024 | | 7 |
| P-056 | | 7 |
| P-067 | | 7 |
| P-025 | | 6 |
| P-080 | | 4 |
| P-123 | | 4 |
| P-048 | | 3 |
| P-040 | | 2 |
| P-006 | | 1 |
| P-004 | | 0 |
| P-015 | | 0 |
| P-083 | | 0 |
| P-047 | | |
| P-129 | | |

TABLE 3

Carcinomas

| Patient No. | Age | Score |
|---|---|---|
| P-064 | | 30 |
| P-103 | | 30 |
| P-104 | | 30 |
| P-108 | | 30 |
| P-101 | | 29 |
| P-102 | | 29 |
| P-099 | | 28 |
| P-107 | | 28 |
| P-110 | | 26 |
| P-098 | | 25 |
| P-134 | | 24 |
| P-062 | | 23 |
| P-090 | | 23 |
| P-095 | | 23 |
| P-093 | | 22 |
| P-100 | | 21 |
| P-122 | | 18 |
| P-084 | | 15 |
| P-109 | | 15 |
| P-118 | | 10 |
| P-138 | | 10 |
| P-091 | | 8 |
| P-096 | | 8 |
| P-053 | | 7 |
| P-119 | | 6 |
| P-117 | | 5 |
| P-105 | | 0 |
| P-097 | | |

As shown above, methods of the invention are effective in screening for the presence of colorectal cancer and adenoma.

Example 6

Neoplasm Detection in Humans

Stool samples were analyzed using the long DNA component of the three component test described in Example 1. Briefly, a single freezer-archived stool sample was assayed in blinded fashion from each of 25 patients with proven supracolonic aerodigestive cancer, 19 patients with colorectal cancer, and 20 colonoscopically-normal controls without history of neoplasia. Human DNA was isolated from stool by sequence-specific hybrid capture, and selected primers were used to amplify long DNA of 1800-2400 bp on each of 5 gene loci (apoptotic DNA consists of short fragment lengths of 180-200 bp and would not be included in this assay). PCR product intensities were determined by UV transilluminator photo-imaging of ethidium bromide stained gels.

In a logistic regression model, long DNA proved to be a discriminating marker for all aerodigestive cancers with an area of 0.83 under the ROC curve. At a specificity of 96% (95% CI:78-99%): sensitivity for all aerodigestive cancers was 77% (95% CI:62-89%); sensitivity for supracolonic aerodigestive cancers was 76% (95% CI:55-91%)—lung 7/8 (88%), esophageal 2/3 (67%), gastroduodenal 1/4 (25%), pancreatic 6/7 (86%), and biliary 3/3 (100%); and sensitivity for colorectal cancers was 79% (95% CI:54-94%). For supracolonic aerodigestive cancers, 5/8 (63%) stage I-II and 12/15 (80%) stage III-IV lesions were detected; staging unknown in 2. For colorectal cancers, 7/10 (70%) stage I-II and 8/9 (89%) stage III-IV lesions were detected.

These observations indicate that supracolonic aerodigestive neoplasms at any aerodigestive tissue site can be detected using DNA markers to analyze stool. The high yield by long DNA also indicates that non-apoptotic exfoliation is a hallmark of most aerodigestive cancers. Larger clinical studies targeting neoplasm-specific nucleic acid markers in stool can be used in this noninvasive screening approach to detect supracolonic aerodigestive neoplasms.

Example 7

A Blind Study

Stool samples are collected from 100 cases with known primary aerodigestive cancers located proximal to the colon (20 lung, 20 esophageal, 20 stomach, 20 pancreas, and 20 bile duct) and from 50 controls (10 colorectal cancers with positive three component test results and 40 healthy colonoscopy-negative patients from a parallel study). Stool samples are assayed in blinded fashion using the three component test described in Example 1. In those cases from which adequate tissue is available from the primary tumor, tissue DNA is also assayed in blinded fashion using the three component test described in Example 1.

Human subjects are instructed to collect a single whole stool using a plastic bucket-type container that mounts on the toilet seat and that is sealed with an airtight lid. Stools are sent to the laboratory so that less than 12 hours elapse between collection and receipt. Upon receipt, stools are bisected and promptly frozen at −80° C. In those instances where either frozen or formalin fixed tissue from the primary tumor is available, tumor DNA is extracted using standard techniques. Tumor DNA samples are labeled differently than stool samples from corresponding patients so that a blind is maintained.

The three component test described in Example 1 is used as follows. Briefly, DNA is recovered from a fecal aliquot less than six grams by solvent extraction (which yields human DNA in essentially 100% of instances). Using quantitative PCR methods: 23 high-frequency point mutations are targeted on K-ras, APC, and p53 genes; BAT-26, a marker for microsatellite instability is assayed; and selected primers are used to detect "long DNA" which includes fragment lengths greater than 270 base pairs and which can reflect non-apoptotic DNA. For each component, results are expressed as percent altered:wild-type. Thus, quantitative distributions are plotted for each assay component for each tumor site group and compared to the control distribution. Results are also reported as a discrete positive or negative value if a cut-off level is chosen; results have generally been considered positive for colorectal neoplasia detection if any DNA alteration was detected at a ratio greater than 1% on replicate testing.

Using the extra (discard) blood drawn for routine laboratory testing, 5-10 mL is retrieved. Serum and buffy-coat is prepared from each sample and stored for future analysis. DNA recovered from these sera is assayed using the three component test, and the buffy coats are evaluated for the presence of tumor cells using an RT-PCR technique.

Frequency distributions of the three component test results (for each compound and for combined components) are tabulated for each tumor site group and for all groups in aggregate. A sample size of 20 in each tumor site group in this study will yield 95% confidence intervals of 6-44%, 12-54%, and 27-73% if the observed detection rates are 20, 30, and 50%, respectively.

A chance-corrected measure of agreement (kappa statistic, and 95% confidence intervals) is computed to estimate the concordance in results between corresponding stool and tissues for those cases in whom both stool and tissue were obtained. This estimate is calculated overall and for each tumor site group.

The patient population is consenting patients with an established primary cancer in the lung or tracheobronchial tree (n=20), esophagus (n=20), stomach (n=20), pancreas (n=20), and bile duct (n=20). Cases are selected sequentially from eligible pools for each site group; gender and age will reflect the referral population. In this study, patients are not stratified within tumor site at the time of selection based on histologic type or other tumor variables. Controls include 10 colorectal cancer patients (positive controls) and 40 asymptomatic patients found to have a normal colonoscopy (negative controls) in a parallel screening study. The inclusion criteria are (1) signed consent, (2) age greater than 18 years, and (3) histologically confirmed primary tumor at appropriate anatomic site. The exclusion criteria include (1) known second primary aerodigestive cancer or premalignant adenoma greater than 1 cm outside of the site of the index cancer, (2) cathartic bowel preparation, barium x-rays, CT scan with oral contrast, or colonoscopy within 7 days, and (3) ostomy or less than ½ colorectum remaining.

The three component test described in Example 1 will detect a proportion of cancers from each proximal aerodigestive site. Correlation of results between corresponding stool and tissue will help determine to what extent mutant DNA expressed by tumors survives enteric transit and can be recovered in stool.

Example 8

In this example a portion of the results from Example 6 relating to the supracolonic aerodigestive neoplasm patients are represented as follows. Methods of the invention were used to detect supracolonic aerodigestive neoplasms in 28 patients.

A stool sample was obtained from each of the 28 patients. The sample was prepared as described above. Fragments of the 5 different loci referred to above were amplified using primers spaced 200, 400, 800, 1300, 1800, and 2400 base pairs apart using the protocol described above in Example 4. Each amplification was scored such that successful amplification of a fragment received a score of 1, and no amplification received a score of 0. Since five loci were interrogated using 6 primer pairs each, the maximum obtainable score was 30 (successful amplification of all 6 fragments at all five loci). A score of 21 was used as a cutoff between diseased and non-diseased patients. The results are shown below.

TABLE 4

Supracolonic Aerodigestive Cancers

| Patient No. | Supracolonic Aerodigestive Cancer | Age | Score |
|---|---|---|---|
| P-145 | Pancreas | 68 | 30 |
| P-164 | Lung CA | 68 | 30 |
| P-166 | Bile Duct | 52 | 30 |
| P-189 | Bile Duct | 43 | 30 |
| P-190 | Lung CA | 50 | 30 |
| P-019 | Atypical Findings in Stomach | 71 | 29 |
| P-152 | Lung CA | 77 | 28 |
| P-167 | Pancreas | 72 | 28 |
| P-011 | Lung CA | 73 | 27 |
| P-153 | Pancreas | 65 | 27 |
| P-165 | Lung CA | 85 | 27 |
| P-170 | Duodenum | 65 | 27 |
| P-182 | Barrett's Esophagus | 58 | 27 |
| P-146 | Bile Duct | 63 | 26 |
| P-081 | Barrett's Esophagus | 74 | 26 |
| P-151 | Pancreas | 49 | 25 |
| P-155 | Lung CA | 60 | 25 |
| P-156 | Lung CA | 57 | 25 |
| P-150 | Pancreas | 78 | 23 |
| P-149 | Esophagus | 59 | 19 |
| P-154 | Esophagus | 80 | 19 |
| P-169 | Pancreas | 71 | 19 |
| P-168 | Lung CA | 63 | 18 |
| P-180 | Pancreas | 67 | 13 |
| P-144 | Esophagus | 59 | 9 |
| P-147 | Stomach | 57 | 7 |
| P-148 | Stomach | 69 | 6 |
| P-171 | Esophagus | 76 | 0 |

As shown above, methods of the invention successfully screened 18 out of 27 patients who actually had a supracolonic aerodigestive neoplasm. Only one patient was misdiagnosed as having cancer when he did not. Thus, the methods of the invention are useful for non-invasive diagnosis of supracolonic aerodigestive neoplasm in a patient.

The threshold of 21 for a positive screen can be changed to accommodate desired sensitivities and specificities. For example, if 18 were determined to be the cutoff, the false negative results shown in Table 4 would be avoided. The skilled artisan knows how to set thresholds depending on the patient (e.g., a lower threshold for patients with symptoms than patients presenting with no symptoms), the disease being diagnosed, and the desired level of sensitivity and specificity. Regardless of the threshold, the principle of the invention remains that long DNA can be used to detect supracolonic aerodigestive neoplasms.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting a supracolonic aerodigestive neoplasm in a mammal, said method comprising:

detecting the presence of long DNA greater than 250 base pairs in length in a stool sample obtained from a mammal, wherein an amount of long DNA greater than 250 base pairs is indicative of a supracolonic aerodigestive neoplasm, wherein an amount of long DNA greater than 250 base pairs is an amount greater than expected to be present in a stool sample obtained from a mammal who does not have cancer, and wherein the sequence or identity of the long DNA is not in itself indicative of supracolonic aerodigestive neoplasm; and performing at least one additional cancer screening technique to detect a location of the supracolonic aerodigestive neoplasm present in the mammal.

2. The method of claim 1, wherein said supracolonic aerodigestive neoplasm comprises a premalignant neoplasm.

3. The method of claim 1, wherein said supracolonic aerodigestive neoplasm comprises a malignant neoplasm.

4. The method of claim 1, wherein said supracolonic aerodigestive neoplasm is selected from the group consisting of lung, naso-oro-pharyngeal, esophageal, stomach, liver, bile duct, gall bladder, small intestine, and pancreas neoplasms.

5. The method of claim 1, wherein said mammal is a human.

6. The method of claim 1, wherein said long DNA comprises DNA greater than 300 base pairs in length.

7. The method of claim 1, wherein said long DNA comprises DNA greater than 400 base pairs in length.

8. The method of claim 1, wherein said long DNA comprises DNA greater than 500 base pairs in length.

9. The method of claim 1, wherein said long DNA comprises DNA greater than 1000 base pairs in length.

10. The method of claim 1, wherein said method further comprises detecting at least one additional neoplasm-specific marker indicative of a neoplasm in said stool sample.

11. The method of claim 10, wherein said at least one additional neoplasm-specific marker is selected from the group consisting of nucleic acid markers, polypeptide markers, and cell markers.

12. The method of claim 10, wherein said at least one additional neoplasm-specific marker is a neoplasm-specific nucleic acid marker.

13. The method of claim 12, wherein said neoplasm-specific nucleic acid marker is selected from the group consisting of nucleic acid having a point mutation and a nucleic acid that reflects microsatellite instability.

14. The method of claim 1, wherein said long DNA comprises DNA greater than 800 base pairs in length.

15. The method of claim 1, wherein said long DNA comprises DNA greater than 1500 base pairs in length.

16. The method of claim 1, wherein said long DNA comprises DNA greater than 1.8 Kb in length.

17. The method of claim 1, wherein said long DNA comprises DNA greater than 2500 base pairs in length.

* * * * *